| | | |
|---|---|---|
| RTA | IFPKQYPIINFTTAGATVQSYTNFIRAVRGRLTTGADVRHEIPVLPNRVG | 50 |
| GELONIN | GLD----TVSESTKGATYITYVNFLNELRVKLKPEGN-SHGIPLLRKKCD | 45 |
| | * | |
| RTA | LPINQRFILVELSNHAELSVTLALDVTNAYVVGYRAGNSAYFFHPDNQED | 100 |
| GELONIN | DP-GKCFVLVALSNDNGQLAEIAIDVTSVYVVGYQVRNRSYFF----KDA | 90 |
| | * | |
| RTA | AEAITHLFTDVQNRYTFAFGGNYDRLEQLAGNLRENIELGNGPLEEAISA | 150 |
| GELONIN | PDAAYEGLFKNTIKTRLHFGGTYPSLEG-EKAYRETTDLGIEPLRIGIKK | 139 |
| | * | |
| RTA | LYYYSTGGTQLPTLARSFIICIQMISEAARFQYIEGEMRTRIRYNRRSAP | 200 |
| GELONIN | LDENAIDNYKPTEIASSLLVVIQMVSEAARFTFIENQIRNN--FQQRIRP | 187 |
| | ** * | |
| RTA | DPSVITLENSWGRLSTAIQESN-QGAFASPIQLQRRNGSKFSVYDVSILI | 249 |
| GELONIN | ANNTISLENKWGKLSFQIRTSGANGMFSEAVELERANGKKYYVTAVDQVK | 237 |
| | * | |
| RTA | PIIALMVYRCAPPPSSQF | 267 |
| GELONIN | PKIALLKFVDKDPK | 251 |

United States Patent [19]
Bernhard et al.
[11] Patent Number: 5,376,546
[45] Date of Patent: Dec. 27, 1994
[54] ANALOGS OF RIBOSOME-INACTIVATING PROTEINS
[75] Inventors: Susan L. Bernhard, Menlo Park; Marc D. Better, Los Angeles; Steve F. Carroll, Walnut Creek; Jul

FIG. 1

```
RTA   I------FPKQYPIINFTTAGATVQSYTNFIRAVRGRLTTGADVRHEIPV        44
                                 *
BRIP  AAKMAKNVDKPLFTATFNVQASSAD-YATFIAGIRNKLRNPAHFSHNRPV        49

RTA   LPN-RVGLPINQRFILVELSNHAELSVTLALDVTNAYVVGYRAGNSAYFF        93
                                                  *
BRIP  LPPVEPNVPPSRWFHVVLKASPTSAGLTLAIRADNIYLEGFKSSDGTWME        99

RTA   HPDNQEDAEAITHLFTDVQNRYTFAFGGNYDRLEQLAGNLRENIELGNGP       143
                                              *
BRIP  LTPGLIPGATYV---------GFGGTYRDLLGDTDKL-TNVALGRQQ          136

RTA   LEEAISALY----YYSTGGTQLPTLARSFIICIQMISEAARFQ----YIE       185
      *                                         * *
BRIP  LADAVTALHGRTKADKASGPKQQQAREAVTTLVLMVNEATRFQTVSGFVA       186

RTA   GEMRTRIRYNRRSAPDPSVITLENSWGRLSTAIQESNQGAFASPIQLQRR       235
                                              *
BRIP  GLLHPKAVEKKSGKIGNEMKAQVNGWQDLSAALLKTDVKPPPGKSPAKFA       236

RTA   NGSKFSVYDVSILIPIIALMVYRCAP--------PPSSQF                 267

BRIP  PIEKMGVRTAEQAANTLGILLFVEVPGGLTVAKALELFHASGGK             280
```

```
RTA      IFPKQYPIINFTTAGATVQSYTNFIRAVRGRLTTGADVRHEIPVLPNRVG    50
                                  *
MOMOII   D------VNFDLSTATAKTYTKFIEDFRATLPFSHKV-YDIPLLYSTIS    42

RTA      LPINQRFILVELSNHAELSVTLALDVTNAYVVGYRAGNSAYFFHPDNQED   100
                                       *
MOMOII   --DSRRFILLDLTSYAYETISVAIDVTNVYVVAYRTRDVSYFF---KESP    87

RTA      AEAITHLFTDVQNRYTFAFGGNYDRLEQLAGNLRENIELGNGPLEEAISA   150
                                            *
MOMOII   PEAYNILFKGTR-KITLPYTGNYENLQTAAHKIRENIDLGLPALSSAITT   136

RTA      LYYYSTGGTQLPTLARSFIICIQMISEAARFQYIEGEMRTRIRYNRRSAP   200
                                 * *
MOMOII   LFYYNAQSA-----PSALLVLIQTTAEAARFKYIERHVAKYVATNFK--P   179

RTA      DPSVITLENSWGRLSTAI--QESNQGAFASPIQLQRRNGSKFSVYDVS--   246
             *
MOMOII   NLAIISLENQWSALSKQIFLAQNQGGKFRNPVDLIKPTGERFQVTNVDSD   229

RTA      ILIPIIALMVYRCAPPPSSQF                               267

MOMOII   VVKGNIKLLLNSRASTADENFITTMTLLGESVVN                  263
```

```
RTA       IFPKQYPIINFTTAGATVQSYTNFIRAVRGRLTTGADVRHEIPVLPNRVG  50
                              *       *
LUFFIN    D-------VRFSLSGSSSTSYSKFIGDLRKALPSNGTVYNLTILLSSASG  43

RTA       LPINQRFILVELSNHAELSVTLALDVTNAYVVGYRAGNSAYFFHPDNQED  100
                                       *
LUFFIN    ---ASRYTLMTLSNYDGKAITVAVDVSQLYIMGYLVNSTSYFF---NESD  87

RTA       AEAITHLFTDVQNRYTFAFGGNYDRLEQLAGNLRENIELGNGPLEEAISA  150
                                *                    *
LUFFIN    AKLASQYVFKGSTIVTLPYSGNYEKLQTAAGKIREKIPLGFPALDSALTT  137

RTA       LYYYSTGGTQLPTLARSFIICIQMISEAARFQYIEGEMRTRIRYNRRSAP  200
                                    ** *
LUFFIN    IFHYDSTAA-----AAAFLVILQTTAEASRFKYIEGQIIERI--SKNQVP  180

RTA       DPSVITLENS-WGRLSTAIQ--ESNQGAFASPIQLQRRNGSKFSVYDVSI  247
                     *
LUFFIN    SLATISLENSLWSALSKQIQLAQTNNGTFKTPVVITDDKQQRVEITNVTS  230

RTA       LIPIIALMVYRCAPPPSSQF                                267
LUFFIN    KVVTKNIQLLLNYKQNVA                                  248
```

FIG. 4

```
RTA       IFPKQYPIINFTTAGATVQSYTNFIRAVRGRLTTGADVRHEIPVLPNRVG   50
                              *       *
TRICHO    D-------VSFRLSGATSSSYGVFISNLRKALPNERKL-YDIPLL--RSS   40

RTA       LPINQRFILVELSNHAELSVTLALDVTNAYVVGYRAGNSAYFFHPDNQED   100
                                       *
TRICHO    LPGSQRYALIHLTNYADETISVAIDVTNVYIMGYRAGDTSYFF--NEASA   88

RTA       AEAITHLFTDVQNRYTFAFGGNYDRLEQLAGNLRENIELGNGPLEEAISA   150
                                *                   *
TRICHO    TEAAKYVFKDAMRKVTLPYSGNYERLQTAAGRIRENIPLGLPALDSAITT   138

RTA       LYYYSTGGTQLPTLARSFIICIQMISEAARFQYIEGEMRTRIRYNRRSAP   200
                                    ** *
TRICHO    LFYYNANSA-----ASALMVLIQSTSEAARYKFIEQQIGSRV--DKTFLP   181

RTA       DPSVITLENSWGRLSTAIQ--ESNQGAFASPIQLQRRNGSKFSVYDV--S   246
                    *
TRICHO    SLAIISLENSWSALSKQIQIASTNNGQFESPVVLINAQNQRVTITNVDAG   231

RTA       ILIPIIALMVYRCAPPPSSQF                                267
TRICHO    VVTSNIALLLNRNNMA                                     247
```

FIG. 5

```
RTA      IFPKQYPIINFTTAGATVQSYTNFIRAVRGRLTTGADVRHEIPVLPNRVG   50
                             *       *
MOMOI    D-------VSFRLSGADPRSYGMFIKDLRNALPFREKVYNIPLLLPSVSG   43

RTA      LPINQRFILVELSNHAELSVTLALDVTNAYVVGYRAGNSAYFFHPDNQED  100
                                      *
MOMOI    ---AGRYLLMHLFNYDGKTITVAVDVTNVYIMGYLADTTSYFFNEPAAEL   90

RTA      AEAITHLFTDVQNRYTFAFGGNYDRLEQLAGNLRENIELGNGPLEEAISA  150
                               *                    *
MOMOI    ASQ--YVFRDARRKITLPYSGNYERLQIAAGKPREKIPIGLPALDSAIST  138

RTA      LYYYSTGGTQLPTLARSFIICIQMISEAARFQYIEGEMRTRIRYNRRSAP  200
                                   ** *
MOMOI    LLHYDSTAA-----AGALLVLIQTTAEAARFKYIEQQIQERA--YRDEVP  181

RTA      DPSVITLENSWGRLSTAIQ--ESNQGAFASPIQLQRRNGSKFSVYDVSIL  248
                   *
MOMOI    SLATISLENSWSGLSKQIQLAQGNNGIFRTPIVLVDNKGNRVQITNVTSK  231

RTA      IPIIALMVY-------------RCAPPPSSQF                    267
MOMOI    VVTSNIQLLLNTRNIAEGDNGDVSTTHGFSST                    263
```

FIG. 6

```
RTA  IFPKQYPIINFTTAGATVQSYTNFIRAVRGRLTTGADVRHEIPVLPNRVG  50
                         *       *
MAP  A-PTLETIASLDLNNPT--TYLSFITNIRTKVADKTE-----QCTIQKIS  42

RTA  LPINQRFILVELSNHAELSVTLALDVTNAYVVGYRA---GNSAYFFHPDN  97
                                  *
MAP  KTFTQRYSYIDLIVSSTQKITLAIDMADLYVLGYSDIANNKGRAFFFKDV  92

RTA  QEDAEAITHLFTDVQNRYTFAFGGNYDRLEQLAGNLRENIELGNGPLEEA  147
                              *                    *
MAP  TEAVANNFFPGATGTNRIKLTFTGSYGDLEK-NGGLRKDNPLGIFRLENS  141

RTA  ISALYYYSTGGTQLPTLARSFIICIQMISEAARFQYIEGEMRTRIRYNRR  197
                                  ** *
MAP  IVNIY---GKAGDVKKQAKFFLLAIQMVSEAARFKYI-SDKIPSEKYEE-  186

RTA  SAPDPSVITLENSWGRLSTAIQESNQGAFASPIQLQRRNGSKFSVYDVSI  247
                  *
MAP  VTVDEYMTALENNWAKLSTAVYNSKPSTTTATKCQLATSPVTISPWIFKT  236

RTA  LIPIIALMVYRCAPPPSSQF                                267
MAP  VEEIKLVMGLLKSS                                      250
```

FIG. 7

```
RTA     IFPKQYPIINFTTAGATVQSYTNFIRAVRGRLTTGADVRHEIPVLPNRVG    50
                            *       *
PAPS    I-----NTITFDAGNATINKYATFMESLRNEAKDPSLKCYGIPMLPNTNS    45

RTA     LPINQRFILVELSNHAELSVTLALDVTNAYVVGYRAGNSA-----YFFHP    95
                                     *
PAPS    ---TIKYLLVKLQGASLKTITLMLRRNNLYVMGYSDPYDNKCRYHIFNDI    92

RTA     DNQEDAEAITHLFTDVQNRYT--FAFGGNYDRLEQLAG-NLRENIELGNG    142
                                     *
PAPS    KGTEYSDVENTLCPSSNPRVAKPINYNGLYPTLEKKAGVTSRNEVQLGIQ    142

RTA     PLEEAISALYYYSTGGTQLPTLARSFIICIQMISEAARFQYIEGEMRTRI    192
         *                                **  *
PAPS    ILSSDIGKI--SGQGSFTEKIEAKFLLVAIQMVSEAARFKYIENQVKTN-    189

RTA     RYNRRSAPDPSVITLENSWGRLSTAIQESNQGAFASPIQLQRRNGSKFSV    242
                          *
PAPS    -FNRDFSPNDKVLDLEENWGKISTAIHNSKNGALPKPLELKNADGTKWIV    238

RTA     YDVSILIPIIALMVYRCAPPPSSQF                             267
PAPS    LRVDEIKPDVGLLNY--VNGTCQAT                             261
```

FIG. 8

```
RTA    IFPKQYPIINFTTAGATVQSYTNFIRAVRGRLTTGADVRHEIPVLPNRVG    50
                           *       *
SAP6   V-----TSITLDLVNPTAQQYSSFVDKIRNNVKDPNLKYGGTDI--AVIG    43

RTA    LPINQRFILVELSNHAELSVTLALDVTNAYVVGYRAGNS-----AYFFHP    95
                                    *
SAP6   PPSKEKFLRINFQSSRG-TVSLGLKRDNLYVVAYLAMDNTNVNRAYYFRS    92

RTA    DNQEDAEAITHLFTDVQNRYTFAFGGNYDRLEQ-----LAGNLRENIELG    140
                                  *
SAP6   EITSAESTALFPEATTANQKALEYTEDYQSIEKNAQITQGDQSRKELGLG    142

RTA    NGPLEEAISALYYYSTGGTQLPTLARSFIICIQMISEAARFQYIEGEMRT    190
          *                                ** *
SAP6   IDLLSTSMEAV---NKKARVVKDEARFLLIAIQMTAEAARFRYIQNLVIK    189

RTA    RIRYNRRSAPDPSVITLENSWGRLSTAI-QESNQGAFASPIQLQRRNGSK    239
                           *
SAP6   N--FPNKFNSENKVIQFEVNWKKISTAIYGDAKNGVFNKDYDFGFGKVRQ    237

RTA    FSVYDVSILIPIIALMVYRCAPPPSSQF                          267
SAP6   VKDLQMGLL------MYLGKPKSSNEAN                          259
```

FIG. 9

```
            GeLo-1
         T     T      T
         T     T      T
5'-GGCCTCGACACCGTCTCCTTCTCCACCAAGGG-3'
         GT G  T G GAGG TAGG G  A
         A  A  A A A  A  A  A  A
                                   50
                    GeLo-5
5'-TCAACCCGGGCTAGATACCGTGTCATTCTCAACCAAAGGTGCCACTTATATTA-3'
   GGGCTAGATACCGTGTCATTCTCAACCAAAGGTGCCACTTATATTACCTACGTGAATTTCTT
    G  L  D  T  V  S  F  S  T  K  G  A  T  Y  I  T  Y  V  N  F  L
                                                   20
                                          100
GAATGAGCTACGAGTTAAATTGAAACCCGAAGGTAACAGCCATGGAATCCCATTGCTGCGC
 N  E  L  R  V  K  L  K  P  E  G  N  S  H  G  I  P  L  L  R
                                                         40
                          150
AAAAAATGTGATGATCCTGGAAAGTGTTTCGTTTTGGTAGCGCTTTCAAATGACAATGGACAGT
 K  K  C  D  D  P  G  K  C  F  V  L  V  A  L  S  N  D  N  G  Q
           200                                         250
TGGCGGAAATAGCTATAGATGTTACAAGTGTTTATGTGGTGGGCTATCAAGTAAGAAACAGATC
 L  A  E  I  A  I  D  V  T  S  V  Y  V  V  G  Y  Q  V  R  N  R  S
                                              80
```

FIG. 10

```
GeLo-10
CTGAACCCGTAACTTGGTAA-5'
         400
GACTTGGGCATTGAACCATTAAGGATTGGCATCAAGAAACTTGATGAAAATGCGATAGACAATT
 D  L  G  I  E  P  L  R  I  G  I  K  K  L  D  E  N  A  I  D  N
                                    140

450                                    500
ATAAACCAACGGAGATAGCTAGTTCTCTATTGGTTGTTATTCAAATGGTGTCTGAAGCAGCTCG
 Y  K  P  T  E  I  A  S  S  L  L  V  V  I  Q  M  V  S  E  A  A  R
                              160                          5'-AT

ATTCACCTTTATTGAGAACCAAATTAGAAATAACTTTCAACAGAGAATTCGCCCGGCGAATAAT
 F  T  F  I  E  N  Q  I  R  N  N  F  Q  Q  R  I  R  P  A  N  N
                              180

GeLo-12                              550
ACAATCAGCAGCCCTTGAG-3'
         600
ACAATCAGCCCTTGAGAATAAATGGGGTAATAAACTCTCGTTCCAGATCCGGACATCAGGTGCAAATG
 T  I  S  L  E  N  K  W  G  K  L  S  F  Q  I  R  T  S  G  A  N
                              200

FIG. 10 (CONT'D)
```

```
                                                    GELO-5
                                                    G G G
                          3'-TTTTTATAATACAATGACGACA
                                    C C G G T T T
                                          C C C
          650
GAATGTTTTCGGAGGCAGTTGAATTGGAACGTGCAAAAATACTATGTCACCGCAGT
 G  M  F  S  E  A  V  E  L  E  R  A  N  G  K  K  Y  Y  V  T  A  V
                       220

G
ACTAGTTCA-5'
T  G  C
  C

GELO-14
                          3'-AGCAGCTATTTCTAGGATTATCATG
          700                                        750
TGATCAAGTAAAACCCAAAATAGCACTCTTGAAGTTCGTCGATAAAGATCCTAAAACGAGCCTT
 D  Q  V  K  P  K  I  A  L  L  K  F  V  D  K  D  P  K  T  S  L
                       240

AGCTCTAGT-5'
                   800
GCTGCTGAATTGATAATCCAGAACTATGAGTCATTAGTGGGCTTTGATTAGTACAACTTATTG
 A  A  E  L  I  I  Q  N  Y  E  S  L  V  G  F  D  -
```

FIG. 10 (CONT'D)

```
                    GeLo-7
                    T    T  T
5'-TTTAAGGACGCCCCGACGCCTACGAGGG-3'
     C A T   G G T G G T A
                 A A A   A
                                                          300
TTACTTCTTTAAAGATGCTCCAGATGCTGCTTACGAAGGCCTCTTCAAAACACAATTAAAAC
 Y  F  F  K  D  A  P  D  A  A  Y  E  G  L  F  K  N  T  I  K  T
                                                  100
         GeLo-9                                    GeLo-11
5'-CTTCATTTTGGCGGCACGTATC-3'              3'-CACTTCCGTATATCTCTCTGT-5'

GeLo-8
               5'-CTCGCTGGAAGGTGAGAA-3'
                                                                3'-TGT
                                       350
AAGACTTCATTTTGGGGGCACGTATCCCTCGCTGGAAGGTGAGAAGGCATATAGAGACAACA
 R  L  H  F  G  G  T  Y  P  S  L  E  G  E  K  A  Y  R  E  T  T
                                    120

FIG. 10 (CONT'D)
```

260
TGCTTTTTATATATATTATAGATATGATGCCGGGCCATGTATTGGCCTTCGTAGCTTAAATAAAGG

CATCGAATATTAGCCTCGGTGGTGTATCTACATGCTGTGTTGTAAAACTGCCAATGTTTATGTT

ATCAAACAGAAATTGGCATGAAGTTTCTGTACAAGTGTTCAATAAACTGGGCTATACATGC(A)$_N$

XE-DT
3'-TTTTTTTTTTTTTTTTAGGGTGCATTCGAACGTCGGAGCTC-5
        3'-AGGGTGCATTCGAACGTCGGAGCTC-5'
                XE

FIG. 10 (CONT'D)

```
       10        20        30        40        50        60        70
AATTCCAAAAATATAGCTTTACCTTTTTTTATTCGAGTGTGTATTTCAGGGCCGTTGGCCAGTTTGTC
     OMB2
5'-GCATTACATCCATGGGGCG-3'

80        90       100       110       120       130       140
               NcoI
CGTCTTAGCTTTGCATTACATCCATGGCGAAAGATGGCGAAGAACGTGGACAAGCCGTCTTCACCGC
                          M  A  K  M  A  K  N  V  D  K  P  L  F  T  A 150       160       170       180       190       200       210
GACGTTCAAGGTTCCAGGCCAGTCCGCAGCTACTACGCCACCTTCATCGCCGGCATCCGCAACAAGCTCCGC
 T  F  N  V  Q  A  S  S  A  D  Y  A  T  F  I  A  G  I  R  N  K  L  R 220       230       240       250       260       270       280
AACCCGGCGCACTTCTCCCACAACCGCCCCGTGCTGCCGCCGGTCGAGCCCAACGTCCCGCCGAGCAGGT
 N  P  A  H  F  S  H  N  R  P  V  L  P  P  V  E  P  N  V  P  P  S  R 290       300       310       320       330       340       350
GGTTCCACGTGGTGCTCAAGGCCTCGCCGACCAGCGCCGGGCTCACGCTGGCCATCCGCGCGGACAACAT
 W  F  H  V  V  L  K  A  S  P  T  S  A  G  L  T  L  A  I  R  A  D  N  I

FIG. 11
```

```
360                370         380          390          400         410          420
CTACCTGGAGGGCTTCAAGAGCAGCGACGGCACCTGGTGGGAGCTCACCCCGGGCCTCATCCCCGGCC
 Y  L  E  G  F  K  S  S  D  G  T  W  W  E  L  T  P  G  L  I  P  G  A 430                440         450          460          470         480          490
ACCTACGTCGGGTTCGGCGGCACCTACCGCGACCTCCTCGGCGACACCGACAAGCTAACCAACGTCGCTC
 T  Y  V  G  F  G  G  T  Y  R  D  L  L  G  D  T  D  K  L  T  N  V  A 500                510         520          530          540         550          560
TCGGCCGACAGCAGCTGGGCGGACGCGGTGACCGCCCTCCACGGGCGCACCAAGGCCGACAAGGCCTCCGG
 L  G  R  Q  Q  L  A  D  A  V  T  A  L  H  G  R  T  K  A  D  K  A  S  G 570                580         590          600          610         620          630
CCCGAAGCAGCAGCAGGCGAGGGAGGCGGTGACGACGCTGGTCCTCATGGTGAACGAGGCCACGCGGTTC
 P  K  Q  Q  Q  A  R  E  A  V  T  T  L  V  L  M  V  N  E  A  T  R  F 640                650         660          670          680         690          700
CAGACGGTGTCTGGGTTCGTGGCCGGGTTGCTGCACCCCAAGGCGGTGGAGAAGAAGAGCGGGAAGATCG
 Q  T  V  S  G  F  V  A  G  L  L  H  P  K  A  V  E  K  K  S  G  K  I
```

FIG. 11 (CONT'D)

```
                                                      710                720                730                740                750                760                770
                                                       |                  |                  |                  |                  |                  |                  |
                                                      GCAATGAGATGAAGGCCCAGGTGAACGGGTGAACGGGTGGCAGGACCTGTCCGCGCTGCTGAAGACGGACGTGAA
                                                       G  N  E  M  K  A  Q  V  N  G  W  Q  D  L  S  A  A  L  L  K  T  D  V  K
                                                                                                      SstII 780                790                800                810                820                830                840
                                                       |                  |                  |                  |                  |                  |                  |
                                                      GCCTCCGCGGGAAAGTCGCCAGCGAAGTTCGCGCCGATCGAGAAGATGGGCGTGAGGACGGCTGAACAG
                                                       P  P  P  G  K  S  P  A  K  F  A  P  I  E  K  M  G  V  R  T  A  E  Q

BRIP-270                                5'-CCAAGTGTCTGGA

BRIP-256   5'-TGTCTGTTCGTGGAGGTGCCG-3'

850                860                870                880                890                900                910
                                                       |                  |                  |                  |                  |                  |                  |
                                                      GCCGGCCAACACGCTGGGGATCCTGCTGTTCGTGGAGGTGCCGGGTGGGTTGACGGTGGCCAAGGCGCTGG
                                                       A  A  N  T  L  G  I  L  L  F  V  E  V  P  G  G  L  T  V  A  K  A  L
                                                                 BamHI

GCTGTTCCATGCGA-3'
                                                                                                                              MB4      3'-G
                                                      920                930                940                950                960                970                980
                                                       |                  |                  |                  |                  |                  |                  |
                                                      AGCTGTTCCATGCGAGTGGTGGGAAATAGGTAGTTTTCCAGGTATACCTGCATGGGTACTGTAAAAGTCG
                                                       E  L  F  H  A  S  G  G  K  -
```

FIG. 11 (CONT'D)

```
                                                  XhoI
       BRIP     3'XhO    3'-CACCCTTTATCCATCAAAAGGAGCTCAAGT-5'
GTTCCGCGACCTGACAAGGTACGCACACCCTTTATCAATTGAGCTCTATAG-5'
       |         |         |         |         |         |
      990      1000      1010      1020      1030      1040      1050
AATAAACATGTCACAGAGTGACGGACTGATATAAATAAATAAATAAACATTGCACAGAGTGACATATAAA

|         |
     1060      1070
CAAATAAATAAATAATTAAAAAAAAA
```

FIG. 11 (CONT'D)

```
                                                    50
CGTCCGAAAATGGTGAAATGCTTACTACTTTCTTTTTAATTATGCCATCTTCATTGGTGTTCCTACTG
              M  V  K  C  L  L  L  S  F  L  I  I  A  I  F  I  G  V  P  T
         MOMO-9
5'-GATGTTAACTTCGATTTGTCGA-3'
         MOMO-3
5'-GATGTTAACTTCGATTTGTCAACGGCTAC-3'
                  T       C T
                          G A
                          T

MOMO-5
                            5'-GCCACTGCCAAAAACCTACACAAAATTTATTGA-3'
                                                              100

3'-TAACTTCTAAA
                                                                                      T C G
                                                                                        T
                                                                                        G

CCAAAGGCGATGTTAACTTCGATTTGTCGACTGCCACTGCCAAAAACCTACACAAAATTTATCGAAGATTT
 A  K  G  D  V  N  F  D  L  S  T  A  T  A  K  T  Y  T  K  F  I  E  D  F
             +1
       MOMO-4
ATCCCGATGGGAAGGTAA-5'
G         T  T
          A  G
             C
CAGGGCGACTCTTCCATTTAGCCATAAAGTGTATGATATACCTCTACTGTATTCCACTATTTCCGACTCC
 R  A  T  L  P  F  S  H  K  V  Y  D  I  P  L  L  Y  S  T  I  S  D  S
                                                    200

FIG. 12
```

```
AGACGTTTCATACTACTCCTCGATCTTACAAGTTATGCATATGAAACCATCTCGGTTGCCCATAGATGTGACGA
 R  R  F  I  L  D  L  T  S  Y  A  Y  E  T  I  S  V  A  I  D  V  T
              50                                                                
                                        300
ACGTTATGTTGTGGCGTTATCGCACCCGCGATGTATCCTACTTTTTAAAGAATCTCTCCTGAAGCTTA
 N  V  Y  V  V  A  Y  R  T  R  D  V  S  Y  F  F  F  K  E  S  P  P  E  A  Y
                                                         400
TAACATCCTATTCAAAGGTACGCGGAAAATTACACTGCCATATACCGGTAATTATGAAAATCTTCAAACTG
 N  I  L  F  K  G  T  R  K  I  T  L  P  Y  T  G  N  Y  E  N  L  Q  T
              100

CTGCACACAAAATAAGAGAGAATATTGATCTTGGACTCCCTGCCTTGAGTAGTGCCATTACCACACATTGTT
 A  A  H  K  I  R  E  N  I  D  L  G  L  P  A  L  S  S  A  I  T  T  L  F
                                                                  150
TTATTACAATGCCCAATCTGCTCCTTCTGCATTGCTTGTACTAATCCAGACGACTGCAGAAGCTGCAAGA
 Y  Y  N  A  Q  S  A  P  S  A  L  L  V  L  I  Q  T  T  A  E  A  A  R
     500
```

FIG. 12 (CONT'D)

```
                                              600
TTTAAGTATATCGAGGCGACACGTTGCTAAGTATGTTGCCACTAACTTTAAGCCAAATCTAGCCATCATAA
 F  K  Y  I  E  R  H  V  A  K  Y  V  A  T  N  F  K  P  N  L  A  I  I
                                                                    700
GCTTGGAAAATCAATGGTCTGCTCTCTCCAAACAAATCTTTTTGGGCGCAGAATCAAGGAGGAAAATTTAG
 S  L  E  N  Q  W  S  A  L  S  K  Q  I  F  L  A  Q  N  Q  G  G  K  F  R
                                       200
AAATCCTGTCGACCTTATAAAACCTACCGGGGAACGGTTTCAAGTAACCAATGTTGATTCAGATGTTGTA
 N  P  V  D  L  I  K  P  T  G  E  R  F  Q  V  T  N  V  D  S  D  V  V
                        800
AAAGGTAATATCAAACTCCTGCTGAACTCCAGAGCTAGCACTGCTGATGAAAACTTTATCACAACCATGA
 K  G  N  I  K  L  L  L  N  S  R  A  S  T  A  D  E  N  F  I  T  T  M
                                            250
                                  MOMO-10
                 3'-CCTTAGACAACACTTAACTCATGGAGCTCAACT-5'

CTCTACTTGGGGGAATCTGTTGTGTGAATTGAAAGTTTAATAATCCACCCATATCGAAATAAGGCATGTTCAT
 T  L  L  G  E  S  V  V  N  -
                         900
GAC
```

FIG. 12 (CONT'D)

ANALOGS OF RIBOSOME-INACTIVATING PROTEINS

This application is a continuation-in-part of U.S. patent application Ser. No. 07/787,567 filed on Nov. 4, 1991, now abandoned.

BACKGROUND

The present invention relates, in general, to materials useful as components of cytotoxic therapeutic agents. More particularly, the invention relates to analogs of ribosome-inactivating proteins specifically modified for conjugation to targeting molecules and to polynucleotides encoding ribosome-inactivating proteins and analogs thereof.

Ribosome-inactivating proteins (RIPs) comprise a class of proteins which is ubiquitous in higher plants. RIPs have also been isolated from bacteria. RIPs are potent inhibitors of eukaryotic protein synthesis. The N-glycosidic bond of a specific adenine base is hydrolytically cleaved by RIPs in a highly conserved loop region of the 28S rRNA of eukaryotic ribosomes thereby inactivating translation.

Stirpe et al., *FEBS Lett.*, 195(1,2), 1–8 (1986) groups plant RIPs into two types. Type I proteins each consist of a single peptide chain having ribosome-inactivating activity, while Type II proteins each consist of an A-chain, essentially equivalent to a Type I protein, disulfide-linked to a B-chain having cell-binding properties. Gelonin, dodecandrin, tricosanthin, tricokirin, bryodin, *Mirabilis* antiviral protein (MAP), barley ribosome-inactivating protein (BRIP), pokeweed antiviral proteins (PAPs), saporins, luffins and momordins are examples of Type I RIPs, while ricin and abrin are examples of Type II RIPs. Amino acid sequence information is reported for various ribosome-inactivating proteins. It appears that at least the tertiary structure of active sites is conserved among Type I RIPs, bacterial RIPs and A-chains of Type II RIPs and, in many cases, primary structure homology is also found. Ready et al., *J. Biol. Chem.*, 259(24), 15252–15256 (1984) and other reports suggest that the two types of RIPs are evolutionarily related.

Separated from their natural environment, Type I plant ribosome-inactivating proteins may be particularly suited for use as components of cytotoxic therapeutic agents. A RIP may be conjugated to a targeting agent that will deliver the RIP to a particular cell type in vivo in order to selectively kill those cells. Because some RIPs, such as the Type I RIP gelonin, are only available from scarce plant materials, it is desirable to clone the genes encoding the RIPs to enable recombinant production of the proteins. It is also desirable to develop analogs of the natural proteins which may be easily conjugated to targeting molecules while retaining their natural biological activity because most Type I RIPs have no natural sites (i.e. available cysteine residues) for conjugation to targeting agents.

There thus exists a need in the art for cloned genes encoding ribosome-inactivating proteins and for analogs of ribosome-inactivating proteins which may be easily conjugated to targeting molecules.

SUMMARY OF THE INVENTION

The present invention provides purified and isolated polynucleotides encoding analogs of Type I ribosome-inactivating proteins having a cysteine available for disulfide bonding to targeting molecules. Vectors comprising the polynucleotides and host cells transformed with the vectors are also provided.

Analogs of a Type I plant RIP are defined herein as non-naturally occurring polypeptides that share the ribosome-inactivating activity of the natural protein but that differ in amino acid sequence from the natural protein. Preferred analogs according to the present invention are analogs of Type I plant RIPs each having a cysteine available for disulfide bonding located at a position in its amino acid sequence from the position corresponding to position 251 in SEQ ID NO: 1 to the carboxyl terminal position of the analog. Other preferred analogs according to the invention are Type I RIPs each having a cysteine available for disulfide bonding at a position in the analog that is on the surface of the protein in its natural conformation and that does not impair native folding or biological activity of the ribosome-inactivating protein. Analogs of bacterial RIPs are also contemplated by the present invention.

The present invention provides an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog corresponding to position 259 in SEQ ID No: 1 or at a position in the amino acid sequence in the analog corresponding to a position from the position corresponding to position 251 in SEQ ID NO: 1 to the carboxyl terminal position of the analog.

An analog according to the present invention may be an analog of gelonin. In an analog of gelonin according to the present invention, the cysteine may be at a position in the analog from position 244 to the carboxyl terminal position of the analog, more preferably at a position in the analog from position 247 to the carboxyl terminal position of the analog, and, in these regions, most preferably at position 244, at position 247 or at position 248 of the amino acid sequence of the analog. It is preferred that the gelonin cysteine residues at positions 44 and 50 be replaced with alanine residues.

An analog according to the present invention may be an analog of barley ribosome-inactivating protein. Preferably, a cysteine in such an analog is at a position in the analog from position 256 to the carboxyl terminal position, and more preferably the cysteine is at a position in the amino acid sequence of the analog from position 260 to the carboxyl terminal position of the analog. Most preferably, in these regions, the cysteine is at position 256, at position 270 or at position 277 of the amino acid sequence of the analog.

An analog according to the present invention may be an analog of momordin II.

Analogs according to the present invention may have a cysteine in the amino acid sequence of the analog at a position which corresponds to a position within one amino acid of position 259 of SEQ ID NO: 1. Such an analog may be an analog of gelonin, of barley ribosome-inactivating protein, or of momordin II.

The present invention also provides a polynucleotide encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein, and which cysteine is located at a position in the amino acid sequence of the analog from the position corresponding to position 251 in SEQ ID NO: 1 to the carboxyl terminal position of the analog. The polynucleotide may encode an analog of gelonin, preferably an analog wherein the cysteine is at a position in the amino acid sequence of the analog from position 244 to the carboxyl terminal position of the analog, more preferably wherein the cysteine is at a position in the analog from position 247 to the carboxyl terminal position of the analog, and most preferably the cysteine is at position 244, at position 247 or at position 248 of the amino acid sequence of the analog. It is preferred that a polynucleotide according to the present invention encode a gelonin analog wherein the native gelonin cysteine residues at positions 44 and 50 are replaced with alanine residues.

A polynucleotide according to the present invention may encode an analog of barley ribosome-inactivating protein, preferably an analog wherein the cysteine is at a position in the analog from position 256 to the carboxyl terminal position of the analog, more preferably wherein the cysteine is at a position in the analog from position 260 to the carboxyl terminal position of the analog, and most preferably wherein the cysteine is at position 256, at position 270 or at position 277 of the amino acid sequence of the analog.

A polynucleotide according to the present invention may encode an analog of mormordin II.

The present invention provides a vector including a polynucleotide encoding an analog of a Type I ribosome-inactivating protein, which analog has a cysteine available for intermolecular disulfide bonding at a amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

The present invention further provides a host cell including a DNA vector encoding an analog of a Type I ribosome-inactivating protein, which analog has a cysteine available for intermolecular disulfide bonding at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog. In such a host cell the vector may encode an analog of gelonin, especially an analog wherein the cysteine is at position 247 of the amino acid sequence of the analog, such as in the host cell deposited as A.T.C.C. Accession No. 69009.

A host cell according to the present invention may include a vector encoding barley ribosome-inactivating protein, especially a host cell wherein the cysteine is at position 277 of the amino acid sequence of the analog such as in the host cell deposited as A.T.C.C. Accession No. 68722.

The present invention also provides an agent toxic to a cell including an analog of a Type I ribosome-inactivating protein linked by a disulfide bond through a cysteine to a molecule which specifically binds to the cell, which cysteine is at an amino acid position in the analog corresponding to a position not naturally available for intermolecular disulfide bonding in the Type I ribosome-inactivating protein and which cysteine is located in the amino acid sequence of the analog from the position corresponding to position 251 in SEQ ID NO: 1 to the carboxyl terminal position of the analog. The agent may include an analog of gelonin, preferably an analog wherein the cysteine is at a position in the analog from position 247 to the carboxyl terminal position of the analog, and more preferably wherein the cysteine is at position 247 or 248 of the amino acid sequence of analog. An agent including an analog wherein the native gelonin cysteine residues at positions 44 and 50 are replaced with alanine residues is preferred.

An agent according to the present invention may include an analog of barley ribosome-inactivating protein, preferably an analog wherein the cysteine is at a position in the analog from position 260 to the carboxyl terminal position of the analog, more preferably wherein the cysteine is at a position in the analog from position 270 to the carboxyl terminal position of the analog, and most preferably wherein the cysteine is at position 256, at position 270 or at position 277 of the amino acid sequence of the analog.

An agent according to the present invention may include an analog of momordin II.

The present invention provides an agent wherein the Type I ribosome-inactivating protein is linked to an antibody, particularly to an H65 antibody or to an antibody fragment, more particularly to an antibody fragment selected from the group consisting of chimeric and human engineered antibody fragments, and most particularly to a Fab antibody fragment, a Fab' antibody fragment or a F(ab')$_2$ antibody fragment. It is highly preferred that an agent according to the present invention include a chimeric or human engineered antibody fragment selected from the group consisting of a Fab antibody fragment, a Fab' antibody fragment and a F(ab')$_2$ antibody fragment.

A method according to the present invention for preparing an analog of a Type I ribosome-inactivating protein includes the step of expressing in a suitable host cell a polynucleotide encoding a Type I ribosome-inactivating protein having a cysteine available for intermolecular disulfide bonding substituted (e.g., by site-directed mutagenesis of the natural DNA sequence encoding the RIP or by chemical synthesis of a DAN sequence encoding the RIP analog) at an amino acid position corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

A product according to the present invention may be a product of a method including the step of expressing in a suitable host cell a polynucleotide encoding a Type I ribosome-inactivating protein having a cysteine available for intermolecular disulfide bonding substituted at an amino acid position corresponding to a position not naturally available for intermolecular disulfide bonding in the Type I ribosome-inactivating protein, which cysteine is located at a position in the amino acid sequence of the analog from the position corresponding to position 251 in SEQ ID NO: 1 to the carboxyl terminal position of the analog.

The present invention provides a method for preparing an agent toxic to a cell including the step of linking an analog of a Type I ribosome-inactivating protein through a cysteine to a molecule which specifically binds to the cell, which analog has the cysteine at an amino acid position corresponding to a position not naturally available for intermolecular disulfide bonding in the Type I ribosome-inactivating protein and which cysteine is located at a position in the amino acid sequence of the analog from the position corresponding to position 251 in SEQ ID NO: 1 to the carboxyl terminal position of the analog.

According to the present invention, a method for treating a disease in which elimination of particular cells is a goa; may include the step of administering to a patient having the disease a therapeutically effective amount of an agent toxic to the cells including an analog of a Type I ribosome-inactivating protein linked through a cysteine to a molecule which specifically binds to the cell, the analog having the cysteine at an amino acid position corresponding to a position not naturally available for intermolecular disulfide bonding in the Type I ribosome-inactivating protein and the cysteine being located at a position in the amino acid sequence of the analog from the position corresponding to position 251 in SEQ ID NO: 1 to the carboxyl terminal position of the analog.

The present invention also provides an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

Such an analog may be an analog wherein the Type I ribosome inactivating protein is gelonin, and is preferably an analog of gelonin wherein the cysteine is at position 10 of the amino acid sequence of the analog as encoded in a vector in a host cell deposited as A.T.C.C. Accession No. 69008. Other such gelonin analogs include those wherein the cysteine is at a position 60 in the amino acid sequence of the gelonin analog.

The present invention further provides an analog of a Type I ribosome-inactivating protein wherein the analog includes only a single cysteine. Such an analog may be an analog of gelonin and is preferably an analog wherein the single cysteine is at position 10, position 44, position 50 or position 247 in the amino acid sequence of the analog, but the cysteine may be located at other positions defined by the invention as well.

The present invention provides a polynucleotide encoding an analog of a Type I ribosome-inactivating protein, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

According to the present invention, a method for preparing an analog of a Type I ribosome-inactivating protein may include the step of expressing in suitable host cell a polynucleotide encoding a Type I ribosome-inactivating protein having a cysteine available for intermolecular disulfide bonding substituted at an amino acid position corresponding to a position not naturally available for disulfide bonding in the Type I ribosome-inactivating protein, the cysteine is located at a position corresponding to an amino acid position on the surface of ricin A-chain in its natural conformation and which analog retains ribosome-inactivating activity of the Type I ribosome-inactivating protein.

The present invention provides an agent toxic to a cell including an analog of a Type I ribosome-inactivating protein linked by a disulfide bond through a cysteine to a molecule which specifically binds to the cell, wherein the analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and wherein the analog retains ribosome-inactivating activity of the Type I ribosome-inactivating protein.

A method according to the present invention for preparing an agent toxic to a cell may include the step of linking an analog of a Type I ribosome-inactivating protein through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

A method according to the present invention for treating a disease in which elimination of particular cells is a goal includes the step of administering to a patient having the disease a therapeutically effective amount of an agent toxic to the cells wherein the agent includes an analog of a Type I ribosome-inactivating protein linked by a disulfide bond through a cysteine to a molecule which specifically binds to the cell, which analog has a cysteine available for intermolecular disulfide bonding located at an amino acid position corresponding to a position not naturally available for intermolecular disulfide bonding in the Type I ribosome-inactivating protein and corresponding to a position on the surface of ricin A-chain in its natural conformation, and which analog retains ribosome-inactivating activity of the Type I ribosome-inactivating protein.

The present invention also provides a purified and isolated polynucleotide encoding natural sequence gelonin, and a host cell including a vector encoding gelonin of the type deposited as A.T.C.C. Accession No. 68721.

The present invention further provides a purified and isolated polynucleotide encoding natural sequence barley ribosome-inactivating protein, and a purified and isolated polynucleotide encoding momordin II.

The RIP analogs are particularly suited for use as components of cytotoxic therapeutic agents and, more specifically, as components of immunotoxins. Cytotoxic agents according to the present invention may be used in vivo to selectively eliminate any cell type to which the RIP component is targeted by the specific binding capacity of the second component. To form an immunotoxin, conjugation to monoclonal antibodies, including chimeric and CDR-grafted antibodies, and antibody domains/fragments (e.g., Fab, Fab', F(ab')$_2$, single chain antibodies, and Fv or single variable domains) as well as conjugation to monoclonal antibodies genetically engineered to include free cysteine residues are within the scope of the present invention. Examples of Fab' and F(ab')2 fragments useful in the present invention are described in copending, co-owned U.S. patent application Ser. No. 07/714,175,filed June 14, 1991, now abandoned which is incorporated by reference herein. RIPs according to the present invention may also be conjugated to targeting agents other than antibodies, for example, lectins which bind to cells having particular surface carbohydrates or hormones which bind specifically to cells having particular receptors.

Cytotoxic agents according to the present invention are suited for treatment of diseases where the elimination of a particular cell type is a goal, such as autoimmune disease, cancer and graft-versus-host disease. The cytotoxic agents are also suited for use in causing immunosuppression and in treatment of infections by viruses such as the Human Immunodeficiency Virus.

Specifically illustrating polynucleotide sequences according to the present invention are the inserts in the plasmid pING3731 in *E. coli* MC1061 (designated strain G274) and in the plasmid pING3803 in *E. coli* E104 (designated strain G275), both deposited with the American Type Culture Collection (A.T.C.C.), Rockville, Md., on Oct. 2, 1991, and assigned A.T.C.C. Accession Nos. 68721 and 68722, respectively. Additional polynucleotide sequences illustrating the invention are the inserts in the plasmid pING3746 in *E. coli* E104 (designated strain G277) and in the plasmid pING3737 in *E. coli* E104 (designated strain G276), which were both deposited with the A.T.C.C. on Jun. 9, 1992, and were respectively assigned Accession Nos. 69008 and 69009.

BRIEF DESCRIPTION OF THE DRAWINGS

FIG. 1 is a computer-generated alignment of the amino acid sequence of the ricin A-chain (RTA) (SEQ ID NO: 1) with the amino acid sequence of the Type I ribosome-inactivating protein gelonin (SEQ ID NO: 2), wherein starred positions indicate amino acids invariant among the ricin A-chain and the Type I RIPs;

FIG. 2 is a computer-generated alignment of the amino acid sequence of the ricin A-chain (SEQ ID NO: 1) with the amino acid sequence of the Type I ribosome-inactivating protein BRIP (SEQ ID NO: 3), wherein starred positions indicate amino acids invariant among the ricin A-chain and the Type I RIPs;

FIG. 3 is a computer-generated alignment of the amino acid sequence of the ricin A-chain (SEQ ID NO: 1) with the amino acid sequence of the Type I ribosome-inactivating protein momordin II (MOMOII) (SEQ ID NO: 4), wherein starred positions indicate amino acids invariant among the ricin A-chain and the Type I RIPs;

FIG. 4 is a computer-generated alignment of the amino acid sequence of the ricin A-chain (SEQ ID NO: 1) with the amino acid sequence of the Type I ribosome-inactivating protein luffin (SEQ ID NO: 5), wherein starred positions indicate amino acids invariant among the ricin A-chain and the Type I RIPs;

FIG. 5 is a computer-generated alignment of the amino acid sequence of the ricin A-chain (SEQ ID NO: 1) with the amino acid sequence of the Type I ribosome-inactivating protein αtrichosanthin (TRICHO) (SEQ ID NO: 6), wherein starred positions indicate amino acids invariant among the ricin A-chain and the Type I RIPs;

FIG. 6 is a computer-generated alignment of the amino acid sequence of the ricin A-chain (SEQ ID NO: 1) with the amino acid sequence of the Type I ribosome-inactivating protein momordin I (MOMOI) (SEQ ID NO: 7), wherein starred positions indicate amino acids invariant among the ricin A-chain and the Type I RIPs;

FIG. 7 is a computer-generated alignment of the amino acid sequence of the ricin A-chain (SEQ ID NO: 1) with the amino acid sequence of the Type I ribosome-inactivating protein *Mirabilis* anti-viral protein (MAP) (SEQ ID NO: 8), wherein starred positions indicate amino acids invariant among the ricin A-chain and the Type I RIPs;

FIG. 8 is a computer-generated alignment of the amino acid sequence of the ricin A-chain (SEQ ID NO: 1) with the amino acid sequence of the Type I ribosome-inactivating protein pokeweed antiviral protein from seeds (PAPS) (SEQ ID NO: 9), wherein starred positions indicate amino acids invariant among the ricin A-chain and the Type I RIPs;

FIG. 9 is a computer-generated alignment of the amino acid sequence of the ricin A-chain (SEQ ID NO: 1) with the amino acid sequence of the Type I ribosome-inactivating protein saporin 6 (SAP6) (SEQ ID NO: 10), wherein starred positions indicate amino acids invariant among the ricin A-chain and the Type I RIPs;

FIG. 10 sets out the DNA and deduced amino acid sequences of the Type I RIP gelonin (SEQ ID NOs: 11 and 2, respectively) as well as indicating the correspondence of oligonucleotide primers utilized for cloning and expression of the gene to the sequences;

FIG. 11 sets out the DNA and deduced amino acid sequences of the Type I RIP BRIP (SEQ ID NOs: 12 and 3, respectively) as well as indicating the correspondence of oligonucleotide primers utilized for cloning and expression of the gene and construction of analogs of the gene to the sequences; and FIG. 12 sets out the DNA and deduced amino acid sequences of the Type I RIP momordin II (SEQ ID NOs: 13 and 4, respectively) as well as indicating the correspondence of oligonucleotide primers utilized for cloning and expression of the gene to the sequences.

DETAILED DESCRIPTION

Nucleotide sequences of genes encoding three plant Type I RIPs and expression vectors containing the genes are provided by the present invention. A first plant RIP, gelonin, is produced by seeds of *Gelonium multiflorum*, a plant of the Euphorbiaceae family native to the tropical forests of eastern Asia, while a second plant RIP, BRIP, is synthesized by the common cereal grain barley. Momordin II, a third plant RIP, is produced in *Momordica balsamina* seeds. Analogs of BRIP are also provided by the present invention. The analogs were genetically engineered to include a cysteine free to participate in a intermolecular disulfide bond and were conjugated to antibody molecules without non-specific chemical derivatization of the RIP with crosslinking agents.

Type I RIP analogs of the present invention offer distinct advantages over the natural proteins for use as components of immunotoxins. Chemical treatment to introduce free sulfhydryl groups in the natural proteins lacking free cysteines typically involves the non-selective modification of amino acid side chains. This non-selectivity often results in antibodies conjugated to different sites on different RIP molecules (i.e., a heterogeneous population of conjugates) and also in a decrease in RIP activity if antibodies are conjugated in or near important regions of the RIP (e.g., the active site or regions involved in translocation across cell membranes). In contrast, RIP analogs according to the present invention can be conjugated to a single antibody through a disulfide bond to a specific residue of the analog resulting in reduced batch to batch variation of the immunoconjugates and, in some cases, immunoconjugates with enhanced properties (e.g., greater cytotoxicity or solubility).

Type I plant RIPs, as well as bacterial RIPs such as shiga and shiga-like toxin A-chains, are homologous to the ricin A-chain and are useful in the present invention.

Type I RIPs may be defined and sites for substitution of a cysteine in a RIP may be identified by comparing the primary amino acid sequence of the RIP to the natural ricin A-chain amino acid sequence, the tertiary structure of which has been described in Katzin et al., *Proteins,* 10, 251–259 (1991), which is incorporated by reference herein.

Amino acid sequence alignment defines Type I RIPs in that the ricin A-chain and the Type I plant RIPs have nine invariant amino acids in common. Based on the ricin sequence the invariant amino acids are tyrosine$_{21}$, arginine$_{29}$, tyrosines$_{80}$, tyrosine$_{123}$, leucine$_{144}$, glutamic acids$_{177}$, alanine$_{178}$, arginine$_{180}$, and tryptophan$_{211}$. The ricin A-chain may be used as a model for the three-dimensional structure of Type I RIPs. A protein lacking a cysteine available for conjugation while having ribosome-inactivating activity and having the nine invariant amino acids when its primary sequence is compared to the primary sequence of the ricin A-chain [according to the alignment algorithm of Myers et al., *CABIOS COMMUNICATIONS,* 4(1), 11–17 (1988), implemented by the PC/GENE program PALIGN (Intelligenetics, Inc., Mountain View, Calif.) and utilizing the Dayhoff Mutation Data Matrix (MDM-78) as described in Schwartz et al., pp. 353–358 in *Atlas of Protein Sequence and Structure,* 5 Supp. 3, National Biomedical Research Foundation, Washington, D.C. (1978)] is defined as a Type I RIP herein and is expected to be useful in the present invention. "Corresponding" refers herein to amino acid positions that align when two amino acid sequences are compared by the strategy of Myers et al., supra.

The primary amino acid sequences of the Type I RIPs gelonin, BRIP, momordin II, luffin [see Islam et al., *Agricultural Biological Chem.,* 54(5), 1343–1345 (199)], α-trichosanthin [see Chow et al., *J. Biol. Chem.,* 265, 8670–8674 (1990)], momordin I [see Ho et al., BBA, 1088, 311–314 (1991)], *Mirabilis* anti-viral protein [see Habuka et al., *J. Biol. Chem.,* 264(12), 6629–6637 (1989)], pokeweed antiviral protein isolated from seeds [see Kung et al., *Agric. Biol. Chem.,* 54(12), 3301–3318 (1990)] and saporin [see Benatti et al., *Eur. J. Biochem.,* 183,465–470 (1989)] are individually aligned with the primary sequence of the ricin A-chain [see Halling et al., *Nucleic Acid Res.,* 13, 8019–8033 (1985)] in FIGS. 1–9, respectively, according to the algorithm of Myers et al., supra, as specified above.

FIGS. 1–9 may be utilized to predict the amino acid positions of the Type I RIPs where cysteine residues may be substituted. Preferred amino acids for cysteine substitution are on the surface of the molecule and include any solvent accessible amino acids that will not interfere with proper folding of the protein if replaced with a cysteine. A region of the ricin A-chain comprising such amino acids is the carboxyl terminal region. Amino acids that should be avoided for replacement are those critical for proper protein folding, such as proline, and those that are solvent inaccessible. Also to be avoided are the nine amino acids invariant among RIPs, and the amino acids in or near regions comprising the active site of ricin A-chain as depicted in FIG. 6 of Katzin et al., supra.

Therefore, a preferred region of substitution for Type I RIPs is their carboxyl terminal region which is solvent accessible and corresponds to the carboxyl terminal region where Type II RIP A-chains and B-chains are naturally linked by a disulfide bond. As shown in the examples, a cysteine may be substituted in positions in the amino acid sequence of a Type I RIP from the position corresponding to position 251 in SEQ ID NO: 1 to the carboxyl terminal position of said Type I RIP, resulting in RIP analogs which retain enzymatic activity and gain disulfide cross-linking capability. One preferred cysteine substitution position is near the position which corresponds to the cysteine at position 259 in the ricin A-chain.

Immunotoxins specifically illustrating the present invention are particularly suited for use in treatment of human autoimmune disease where T-cell function is implicated. Treatment of autoimmune diseases with immunotoxins is described in co-owned U.S. patent application Ser. No. 306,433 filed on Sep. 13, 1991, now abandoned which is incorporated by reference herein. Examples of autoimmune diseases are systemic lupus erythematosus, scleroderma diseases (including lichen sclerosus, morphea and lichen planus), rheumatoid arthritis, chronic thyroiditis, pemphigus vulgaris, diabetes mellitus type 1, progressive systemic sclerosis, aplastic anemia, myasthenia gravis, myositis, Sjogrens disease, Crohn's disease, ulcerative colitis, and primary biliary cirrhosis. Autoimmunity is also implicated in multiple sclerosis, uveitis, psoriasis and Meniere's disease. A general description of various autoimmune diseases may be found in Rose and Mackey, Eds., *The Autoimmune Diseases,* Academic Press (1985).

The immunotoxins may be administered to a patient either singly or in a cocktail containing two or more immunotoxins, other therapeutic agents, compositions, or the like, including, but not limited to, immunosuppressive agents, tolerence-inducing agents, potentiators and side-effect relieving agents. Particularly preferred are immunosuppressive agents useful in suppressing allergic reactions of a host. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexiline, verapamil, amantadine and chloroquine. All of these agents are administered in generally-accepted efficacious dose ranges such as those disclosed in the *Physician's Desk Reference,* 41st Ed., Publisher Edward R. Barnhart, N.J. (1987). Patent Cooperation Treaty (PCT) patent application WO 89/069767 published on Aug. 10, 1989, discloses administration of an immunotoxin as an immunosuppressive agent and is incorporated by reference herein.

Anti-T cell immunotoxins may be formulated into either an injectable or topical preparation. Parenteral formulations are known and are suitable for use in the invention, preferably for intramuscular or intravenous administration. The formulations containing therapeutically-effective amounts of anti-T cell immunotoxins are either sterile liquid solutions, liquid suspensions or lyophilized versions, and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where the biological activity is less than or equal to 20 ng/ml when measured in a reticulocyte lysate assay. Typically, the pharmaceutical compositions containing anti-T cell immunotoxins will be administered in a therapeutically effective dose in a range of from about 0.01 mg/kg to about 5 mg/kg of the patient. A preferred, therapeutically effective dose of the pharmaceutical composition containing anti-T cell immunotoxin will be in a range of from about 0.01 mg/kg to about 0.5 mg/kg body weight of the patient administered over several days to two weeks by daily intravenous infusion, each given over a one hour period, in a sequential patient dose-escalation regimen.

Anti-T cell immunotoxin is formulated into topical preparations for local therapy by including a therapeutically effective concentration of anti-T cell immunotoxin in a dermatological vehicle. The amount of anti-T cell immunotoxin to be administered, and the anti-T cell immunotoxin concentration in the topical formulations, depends upon the vehicle selected, the clinical condition of the patient, the systemic toxicity and the stability of the anti-T cell immunotoxin in the formulation. Thus, a physician knows to employ the appropriate preparation containing the appropriate concentration of anti-T cell immunotoxin in the formulation, as well as the appropriate amount of formulation to administer depending upon clinical experience with the patient in question or with similar patents. The concentration of anti-T cell immunotoxin for topical formulations is in the range of greater than from about 0.1 mg/ml to about 25 mg/ml. Typically, the concentration of anti-T cell immunotoxin for topical formulations is in the range of greater than from about 1 mg/ml to about 20 mg/ml. Solid dispersions of anti-T cell immunotoxin as well as solubilized preparations can be used. Thus, the precise concentration to be used in the vehicle is subject to modest experimental manipulation in order to optimize the therapeutic response. Greater than about 10 mg anti-T cell immunotoxin/100 grams of vehicle may be useful with 1% w/w hydrogel vehicles in the treatment of skin inflammation. Suitable vehicles, in addition to gels, are oil-in-water or water-in-oil emulsions using mineral oils, petroleum and the like.

Anti-T cell immunotoxin is optionally administered topically by the use of a transdermal therapeutic system [Barry, *Dermatological Formulations*, p. 181 (1983) and literature cited therein]. While such topical delivery systems have been designed for transdermal administration of low molecular weight drugs, they are capable of percutaneous delivery. They may be readily adapted to administration of anti-T cell immunotoxin or derivatives thereof and associated therapeutic proteins by appropriate selection of the rate-controlling microporous membrane.

Topical preparations of anti-T cell immunotoxin either for systemic or local delivery may be employed and may contain excipients as described above for parenteral administration and other excipients used in a topical preparation such as cosolvents, surfactants, oils, humectants, emollients, preservatives, stabilizers and antioxidants. Any pharmacologically-acceptable buffer may be used, e.g., Tris or phosphate buffers. The topical formulations may also optionally include one or more agents variously termed enhancers, surfactants, accelerants, adsorption promoters or penetration enhancers, such as an agent for enhancing percutaneous penetration of the anti-T cell immunotoxin or other agents. Such agents should desirably possess some or all of the following features as would be known to the ordinarily skilled artisan: pharmacological inertness, non-promotive of body fluid or electrolyte loss, compatible with anti-T cell immunotoxin (non-inactivating), and capable of formulation into creams, gels or other topical delivery systems as desired.

Anti-T cell immunotoxin may also be administered by aerosol to achieve localized delivery to the lungs. This is accomplished by preparing an aqueous aerosol, liposomal preparation or solid particles containing immunotoxin. Ordinarily, an aqueous aerosol is made by formulating an aqueous solution or suspension of anti-T cell immunotoxin together with conventional pharmaceutically acceptable carriers and stabilizers. The carriers and stabilizers vary depending upon the requirements for the particular anti-T cell immunotoxin, but typically include: nonionic surfactants (Tweens, Pluronics, or polyethylene glycol); innocuous proteins like serum albumin, sorbitan esters, oleic acid, lecithin; amino acids such as glycine; and buffers, salts, sugars or sugar alcohols. The formulations may also include mucolytic agents as well as bronchodilating agents. The formulations are sterile. Aerosols generally are prepared from isotonic solutions. The particles optionally include normal lung surfactants.

Aerosols may be formed of the particles in aqueous or nonaqueous (e.g., fluorocarbon propellant) suspension. Such particles include, for example, intramolecular aggregates of anti-T cell immunotoxin or derivatives thereof or liposomal or microcapsular-entrapped anti-T cell immunotoxin or derivatives thereof. The aerosols should be free of lung irritants, i.e., substances which cause acute bronchoconstriction, coughing, pulmonary edema or tissue destruction. However, nonirritating absorption-enhancing agents are suitable for use herein. Sonic nebulizers are preferably used in preparing aerosols. Sonic nebulizers minimize exposing the anti-T cell immunotoxin or derivatives thereof to shear, which can result in degradation of anti-T cell immunotoxin.

Anti-T cell immunotoxin may be administered systemically, rather than topically, by injection intramuscularly, subcutaneously, intrathecally or intraperitoneally or into vascular spaces, particularly into the joints, e.g., intraarticular injection at a dosage of greater than about 1 μg/cc joint fluid/day. The dose will be dependent upon the properties of the anti-T cell immunotoxin employed, e.g., its activity and biological half-life, the concentration of anti-T cell immunotoxin in the formulation, the site and rate of dosage, the clinical tolerance of the patient involved, the autoimmune disease afflicting the patient and the like, as is well within the skill of the physician.

The anti-T cell immunotoxin of the present invention may be administered in solution. The pH of the solution should be in the range of pH 5 to 9.5, preferably pH 6.5 to 7.5. The anti-T cell immunotoxin or derivatives thereof should be in a solution having a suitable pharmaceutically-acceptable buffer such as phosphate, Tris(hydroxymethyl)aminomethane-HCl or citrate and the like. Buffer concentrations should be in the range of 1 to 100 mM. The solution of anti-T cell immunotoxin may also contain a salt, such as sodium chloride or potassium chloride in a concentration of 50 to 150 mM.

An effective amount of a stabilizing agent such as an albumin, a globulin, a gelatin, a protamine or a salt of protamine may also be included, and may be added to a solution containing anti-T cell immunotoxin or to the composition from which the solution is prepared.

Systemic administration of anti-T cell immunotoxin is made daily and is generally by intramuscular injection, although intravascular infusion is acceptable. Administration may also be intranasal or by other nonparenteral routes. Anti-T cell immunotoxin may also be administered via microspheres, liposomes or other microparticulate delivery systems placed in certain tissues including blood. Topical preparations are applied daily directly to the skin or mucosa and are then preferably occluded, i.e., protected by overlaying a bandage, polyolefin film or other barrier impermeable to the topical preparation.

The following examples illustrate practice of the invention in the cloning of the genes encoding the Type I RIPs gelonin, BRIP and momordin II, and in the production of analogs of gelonin and BRIP and of immunoconjugates of the analogs. The examples are not to be construed as limiting the invention.

Example 1

The cloning of the gelonin gene according to the present invention obviates the requirement of purifying the RIP gene product from its relatively scarce natural source, *G. multiflorum* seeds, and allows development of gelonin analogs conjugatable to antibodies without prior chemical derivatization. One formidable hurdle in the cloning of the gene was that the available *Gelonium* seeds are old and inviable making preparation of intact messenger RNA from the seeds impossible. Cloning the gene from cDNA prepared from messenger RNA was thus impractical and total RNA was utilized to generate cDNA. Using total RNA to make cDNA under normal circumstances, i.e., when mRNA may be utilized, is not desirable because total RNA typically comprises about 95% ribosomal RNA.

Preparation of RNA from G. Multiflorum Seeds

Total RNA was prepared from Gelonium seeds (Dr. Michael Rosenblum, M. D. Anderson Cancer Center, Houston, Tex.) by a modification of the procedure for preparation of plant RNA described in Ausubel et al., eds., *Current Protocols in Molecular Biology*, Wiley & Sons, 1989. Briefly, 4.0 grams of seeds were ground to a fine powder in a pre-cooled (−70° C.) mortar and pestle with liquid $N_2$. The powder was added to 25 ml Grinding buffer (0.18M Tris, 0.09M LiCl, 4.5 mM EDTA, 1% SDS, pH 8.2) along with 8.5 ml of phenol equilibrated with TLE (0.2M Tris, 0.1M LiCl, 5 mM EDTA pH 8.2). The mixture was homogenized using a Polytron PT-1035 (#5 setting). 8.5 ml of chloroform was added, mixed and incubated at 50° C. for 20 minutes. The mixture was centrifuged at 3K for 20 minutes in a rotor precooled to 4° C. and the aqueous phase was transferred to a new tube. 8.5 ml of phenol was added followed by 8.5 ml of chloroform and the mixture was recentrifuged. This extraction was repeated 3 times. The RNA in the aqueous phase was then precipitated by adding ⅓ volume 8M LiCl, and incubated at 4° C. for 16 hours. Next, the RNA was pelleted by centrifugation for 20 minutes at 4° C. The pellet was washed with 5 ml of 2M LiCl, recentrifuged and resuspended in 2 ml of water. The RNA was precipitated by addition of NaOAc to 0.3M and 2 volumes of ethanol. The RNA was stored in 70% ethanol at −70° C.

cDNA Preparation cDNA was prepared from total Gelonium RNA by two similar methods.

The first method involved making a cDNA library in the bacterial expression plasmid pcDNAII using the Librarian II cDNA Library Construction System kit (Invitrogen). About 5 μg of total RNA was converted to first strand cDNA with a 1:1 mixture of random primers and oligo-dT. Second strand synthesis with DNA polymerase I was performed as described by the system manufacturer. Double stranded cDNA was ligated to BstX1 linkers and size fractionated. Pieces larger than about 500 bp were ligated into the expression vector provided in the kit. Individual vectors were introduced into *E. coli* either by transformation into high-efficiency competent cells or by electroporation into electrocompetent cells. Electroporation was performed with a BTX100 unit (BTX, San Diego, Calif.) in 0.56μ Flatpack cells as recommended by BTX based on the method of Dower et al., *Nucleic Acids Res.*, 16, 6127–6145 (1988), at a voltage amplitude of 850 V and a pulse length of 5 mS. The resulting library consisted of approximately 150,000 colonies.

The second method involved generating cDNA using the RNA-PCR kit sold by Perkin-Elmer-Cetuso About 100 ng of total Gelonium RNA was used as template for cDNA synthesis.

Determination of the Gelonin Protein Sequence

The partial sequence of the native gelonin protein was determined by direct amino acid sequence analysis by automated Edman degradation as recommended by the manufacturer using an Applied Biosystems model 470A protein sequencer. Proteolytic peptide fragments of gelonin (isolated from the same batch of seeds as the total RNA) were sequenced.

Cloning of the Gelonin Gene

Three overlapping gelonin cDNA fragments were cloned and a composite gelonin gene was assembled from the three fragments.

(1) Cloning of the Fragment Encoding the Middle Amino Acids of Gelonin in Vector pING3823.

Degenerate DNA primers based on the gelonin partial amino acid sequences were used to amplify by PCR, segments of the cDNA generated with the Perkin-Elmer-Cetus kit. Six primers were designed based on regions of the gelonin amino acid sequence where degeneracy of the primers could be minimized. Appropriate pairs of primers were tested for amplification of a gelonin gene fragment. When products of the expected DNA size were identified as ethidium bromide-stained DNA bands on agarose gels, the DNA was treated with T4 DNA polymerase and then purified from an agarose gel. Only the primer pair consisting of primers designated gelo-7 and gelo-5 yielded a relatively pure product of the expected size. The sequences of degenerate primers gelo-7 and gelo-5 are set out below using IUPAC nucleotide symbols.

Gelo-7 (SEQ ID NO: 14)
5′ TTYAARGAYGCNCCNGAYGCNGCNTAYGARGG 3′

Gelo-5 (SEQ ID NO: 15)
3′ TTYTTYATRATRCANTGNCGNCANCTRGTYCA 5′

Primer gelo-7 corresponds to amino acids 87–97 of gelonin while primer gelo-5 corresponds to amino acids 226–236. The blunt-ended DNA fragment (corresponding to amino acids 87 to 236 of gelonin) generated with primers gelo-7 and gelo-5 was cloned into pUC18 (BRL, Gaithersburg, Md.). The DNA sequence of the insert was determined, and the deduced amino acid sequence based on the resulting DNA sequence matched the experimentally determined gelonin amino acid sequence. The clone containing this gelonin segment is denoted pING3726.

The insert of clone pING3726 was labeled with $^{32}$P and used as a probe to screen the 150,000-member Gelonium cDNA library. Only one clone hybridized to the library plated in duplicate. This clone was purified from the library and its DNA sequence was determined. The clone contains a fragment encoding 185 of the 270 amino acids of gelonin (residues 25-209) and is denoted pING3823.

(2) Cloning of the Fragment Encoding the N-terminal Amino Acids of Gelonin.

Based on the sequence determined for the gelonin gene segment in pING3726, exact oligonucleotide primers were designed as PCR amplification primers to be used in conjunction with a degenerate primer to amplify a 5' gelonin gene fragment and with a nonspecific primer to amplify a 3' gelonin gene fragment. cDNA generated using the Perkin-Elmer-Cetus RNA-PCR kit was amplified.

To amplify the 5'-end of the gelonin gene, PCR amplification with a degenerate primer gelo-1 and an exact primer gelo-10 was performed. The sequences of the primers are set out below.

Gelo-1 (SEQ ID NO: 16)
5' GGNYTNGAYACNGTNWSNTTYWSNACNAARGG 3'

Gelo-10 (SEQ ID NO: 17)
3' TGTCTGAACCCGTAACTTGGTAA 5'

Primer gelo-1 corresponds to amino acids 1-11 of the gelonin gene while primer gelo-10 corresponds to amino acids 126-133. The product from the reaction was re-amplified with gelo-1 (SEQ ID NO: 16) and gelo-11 (an exact primer comprising sequences encoding amino acids 119-125 of gelonin) to confer specificity to the reaction product. The sequence of primer gelo-11 is listed below.

Gelo-11 (SEQ ID NO: 18)
3' CACTCTTCCGTATATCTCTCTGT 5'

Hybridization with an internal probe confirmed that the desired specific gelonin DNA fragment was amplified. This fragment was cloned into pUC18, and the vector generated was designated pING3727. The fragment was sequenced revealing that the region of the fragment (the first 27 nucleotides) corresponding to part of the degenerate primer gelo-1 could not be translated to yield the amino acid sequence upon which primer gelo-1 was originally based. This was not unexpected considering the degeneracy of the primer. The fragment was reamplified from the Gelonium cDNA with exact primers gelo-11 (SEQ ID NO: 18) and gelo-5' (which extends upstream of the 5' end of the gelonin gene in addition to encoding the first 16 amino acids of gelonin). The sequence of primer gelo-5' is set out below.

Gelo-5' (SEQ ID NO: 19)
5' TCAACCCGGGCTAGATACCGTGTCAT
TCTCAACCAAAGGTGCCACTTATATTA 3'

The resulting DNA fragment encodes the first 125 amino acids of gelonin. While the majority of the sequence is identical to the natural gelonin gene, the first 32 nucleotides of the DNA fragment may not be. For the purposes of this application this N-terminal fragment is referred to as fragment GEL1-125.

(3) Cloning of the Fragment Encoding the C-terminal Amino Acids of Gelonin.

To amplify the 3'-end of the gelonin gene as well as 3' untranslated sequences, PCR amplification with exact primers gelo-9 and XE-dT was performed. The sequence of each of the primers is set out below.

Gelo-9 (SEQ ID NO: 20)
5' CTTCATTTTGGCGGCACGTATCC 3'

XE-dT (SEQ ID NO: 21)
3' TTTTTTTTTTTTTTTTTTTTTAG
GGTGCATTCGAACGTCGGAGCTC 5'

Primer gelo-9 corresponds to amino acids 107-113 of gelonin. Primer XE-dT consists of an 3' oligo-dT portion and a 5' portion containing the restriction sites HindIII and XhoI, and will prime any poly A-containing cDNA. The reaction product was reamplified with exact primers gelo-8 and XE. The sequences of primers gelo-8 and XE are set out below.

Gelo-8 (SEQ ID NO: 22)
5' CTCGCTGGAAGGTGAGAA 3'

XE (SEQ ID NO: 23)
3' AGGGTGCATTCGAACGTCGGAGCTC 5'

Primer gelo-8 consists of sequences encoding amino acids 115-120 of gelonin while the primer XE corresponds to the 5' portion of the XE-dT primer which contains HindIII and XhoI restriction sites. Hybridization with internal probes confirmed that the desired gelonin gene fragment was amplified. The fragment was cloned into pUC18 by two different methods. First, it was cloned as a blunt-ended fragment into the SmaI site of pUC18 (the resulting vector was designated pING3728) and, second, it was cloned as an EcoRI to HindIII fragment into pUC18 (this vector was designated pING3729). Both vector inserts were sequenced. The insert of pING3728 encodes amino acids 114-270 of gelonin, while the insert of pING3729 encodes amino acids 184-270 of gelonin plus other 3' sequences.

(4) Assembly of the overlapping gelonin DNA fragments into a composite gelonin gene To reassemble the C-terminal two-thirds of the gelonin gene, vector pING3729 was cut with SspI (one SspI site is located within the vector and the second is located about 80 bp downstream of the termination codon of the insert in the vector) and an XhoI linker (8 bp, New England Biolabs) was ligated to the resulting free ends. The DNA was then cut with XhoI and EcoRI, and the 350 bp fragment generated, encoding amino acids 185-270 of gelonin, was isolated. This 350 bp fragment was ligated adjacent to a NcoI to EcoRI fragment from pING3823 encoding amino acids 37-185 of gelonin in a intermediate vector denoted pING3730, thus reassembling the terminal 87% of the gelonin gene (amino acids 37–270).

Next, fragment GEL1-125 was cut with SmaI and NcoI, resulting in a fragment encoding amino acids 1–36 of gelonin which was ligated along with the NcoI to XhoI fragment of pING3730 into the vector pIC100.

[pIC100 is identical to pING1500 described in Better et al., Science, 240, 1041–1043 (1988), except that it lacks 37 bp upstream of the pelB leader sequence. The 37 bp were eliminated by digestion of pING1500 with SphI and EcoRI, treatment with T4 polymerase and religation of the vector. This manipulation regenerated an EcoRI site in the vector while eliminating other undesirable restriction sites.] Before ligation, the vector pIC100 had previously been digested with SstI, treated with T4 polymerase, and cut with XhoI. The ligation generated a new vector containing a complete gelonin gene that was designated plasmid pING3731 (A.T.C.C. Accession No. 68721). The complete DNA sequence of the gelonin gene is set out in SEQ ID NO: 11 and in FIG. 10.

Construction of Expression Vectors Containing the Gelonin Gene

A first *E. coli* expression vector was constructed containing the gelonin gene linked to the *Erwinia carotovora* pelB leader sequence, and to the *Salmonella typhimurium* araB promoter. A basic vector containing the araB promoter is described in co-owned U.S. Pat. No. 5,028,530 issued Jul. 2, 1991 which is incorporated herein by reference. The vector containing the araB promoter was cut with EcoRI and XhoI. Two DNA fragments were then ligated in tandem immediately downstream of the promoter. The fragment ligated adjacent to the promoter was a 131 bp fragment derived from SstI digestion, T4 polymerase treatment and digestion with EcoRI of the pIC100 vector which includes the leader sequence of the *E. carotovora* pelB gene. The translated leader sequence is a signal for secretion of the respective protein through the cytoplasmic membrane. The fragment ligated downstream of the leader sequence was a SmaI to XhoI fragment from pING3731 which contains the complete gelonin gene. Thus, the expression vector contains the gelonin gene linked to the pelB leader sequence and the arab promoter. This plasmid is designated pING3733.

A second expression vector may be constructed that is identical to the first except that the gelonin gene sequences encoding the nineteen C-terminal amino acids of gelonin are not included. The cDNA sequence of the gelonin gene predicted a 19 residue C-terminal segment that was not detected in any peptide fragments generated for determination of the gelonin amino acid sequence. These 19 amino acids may represent a peptide segment that is cleaved from the mature toxin post-translationally, i.e. that is not present in the native protein. A similar C-terminal amino acid segment was identified in the plant toxin αtrichosanthin [Chow et al., *J. Biol. Chem.*, 265, 8670–8674 (1990)]. Therefore, the expression product without the C-terminal fragment may be of importance.

For construction of a gelonin expression vector without the 19 C-terminal amino acids of gelonin, PCR was used to amplify and alter the 3'-end of the gene. pING3728 was amplified with primers gelo-14 and gelo-9 (SEQ ID NO: 20). The sequence of primer gelo-14 is set out below.

Gelo-14 (SEQ ID NO: 24)
5' TGATCTCGAGTA<u>CTA</u>TTTAGGATCTTTATCGACGA 3'

Primer gelo-14, which corresponds to gelonin amino acids 245–256, introduces a termination codon (underlined in the primer sequence) in the gelonin gene sequence which stops transcription of the gene before the sequences encoding the terminal 19 amino acids of the gelonin and also introduces a XhoI site immediately downstream of the termination codon. The PCR product was cut with XhoI and EcoRI, and the resulting 208 bp fragment encoding amino acids 185–251 of gelonin was purified from an agarose gel. This fragment was ligated adjacent to the NcoI to EcoRI fragment from pING3823 encoding amino acids 37–185 of gelonin to generate plasmid pING3732. A final expression vector, pING3734, containing a gelonin gene with an altered 3'-end was generated by substituting an NcoI to XhoI fragment encoding amino acids 37–251 of gelonin from pING3732 into pING3733.

Identification of the Native Gelonin 5'-End

Inverse PCR was used to identify a cDNA clone encoding the 5'-end of the mature gelonin gene. 5 μg of total *G. multiflorum* RNA was converted to cDNA using the Superscript Plamid System (BRL, Gaithersburg, Md.) with Gelo-11 (SEQ ID NO: 18) as a primer. Gelonin cDNA was self-ligated to generate covalent circular DNA and the ligated DNA was amplified by PCR with oligonucleotides Gelo-9 (SEQ ID NO: 20) and Gelo-16. The sequence of primer Gelo-16 is set out below.

Gelo-16 (SEQ ID NO: 25)
5' GTAAGCAGCATCTGGAGCATCT 3'

The PCR product was size-fractionated on an agarose gel and DNAs larger than 300 bp were cloned into SmaI cut pUC18. Several clones were sequenced with the primer Gelo-18, the sequence of which is set out below.

Gelo-18 (SEQ ID NO: 26)
5' CATTCAAGAAATTCACGTAGG 3'

A clone identified as having the largest gelonin-specific insert was designated pING3826. The DNA sequence of pING3826 included the first 32 nucleotides of the natural, mature gelonin gene not necessarily present in gelonin expression plasmids pING3733 and pING3734. The complete DNA sequence of the natural gelonin gene is set out in SEQ ID NO: 57.

Construction of Expression Vectors Containing a Gelonin Gene with a Natural 5' End Derivatives of expression vectors pING3733 and pING3734 (described above) containing a gelonin gene with the natural 5' sequence were generated as follows. The 5'-end of gelonin was amplified from pING3826 with the PCR primers Gelo-16 (SEQ ID NO: 24) and Gelo-17, the sequence of which is set out below.

Gelo-17 (SEQ ID NO: 27)
5' GGCCTGGACACCGTGAGCTTTAG 3'

The 285 bp PCR product was treated with T4 polymerase and cut with NcoI. The resulting 100 bp 5'-end DNA fragment was isolated from an agarose gel and ligated adjacent to the 120 bp pelB leader fragment from pIC100 (cut with SstI, treated with T4 polymerase and cut with PstI) into either pING3733 or pING3734 digested with PstI and NcoI. The resulting plasmids pING3824 and pING3825 contain the entire native gelonin gene and the native gelonin gene minus the nineteen amino acid carboxyl extension, respectively, linked to the pelB leader and under the transcriptional control of the araB promoter. The gene construct without the nineteen amino acid carboxyl extension in both pING3734 and pING3825 encodes a protein product referred to in this application as "recombinant gelonin."

Assembly of Gelonin Genes with Cysteine Residues Available for Conjugation

The gelonin protein has two cysteine residues at positions 44 and 50 which are linked by an endogenous disulfide bond. The protein contains no free cysteine residue directly available for conjugation to antibodies or other proteins. Analogs of gelonin which contain a free cysteine residue available for conjugation were generated by two different approaches. In one approach, various residues along the primary sequence of the gelonin were replaced with a cysteine residue, creating a series of analogs which contain an odd number of cysteine residues. In another approach, one of the two endogenous cysteines was replaced by alanine, creating a molecule which lacks an intrachain disulfide bond but contains a single, unpaired cysteine.

Eight analogs of gelonin were constructed. Six non-cysteine residues of gelonin were targeted for substitution with a cysteine residue. Comparison of the amino acid sequence of gelonin to the natural amino acid sequence and tertiary structure of the ricin A-chain (see FIG. 1) suggested that these positions would be at the surface of the molecule and available for conjugation. Each of the six gelonin analogs include a cysteine substituted in place of one of the following residues: lysine$_{10}$, asparagine$_{60}$, asparagine$_{239}$, lysine$_{244}$, aspartate$_{247}$, and lysine$_{248}$, and the analogs have respectively been designated Gel$_{C10}$, Gel$_{C60}$, Gel$_{C230}$, Gel$_{C244}$, Gel$_{C247}$, and Gel$_{C248}$.

An analog of gelonin was constructed in which one of the native gelonin cysteines that participates in an endogenous disulfide bond was replaced with a non-cysteine residue. Specifically, the cysteine at position 50 was replaced with an alanine residue, creating a gelonin analog (designated Gel$_{C44}$) which has a cysteine available for disulfide bonding at position 44. The combined series of the foregoing seven analogs thus spans the entire length of the mature gelonin protein.

An eighth gelonin analog was constructed in which both native gelonin cysteines were replaced with alanines. A ninth analog may be constructed that has alanine residues substituted in place of both native cysteines and has a cysteine residue substituted in place of the native aspartate at position 247.

The eight variants of recombinant gelonin were constructed by overlap extension PCR of plasmids pING3734 or pING3825 with synthetic oligonucleotides. The sequences of the primers used for PCR are set out below. In each mutagenic primer sequence, the nucleotides encoding the change to a cysteine or an alanine residue are underlined.

Gelo-11 (SEQ ID NO: 18)

Gelo-16 (SEQ ID NO: 25)

Gelo-17 (SEQ ID NO: 27)

Gelo-18 (SEQ ID NO: 26)

Gelo-9 (SEQ ID NO: 20)

GeloC-1 (SEQ ID NO: 28)
5' TCGATT<u>GC</u>GATCCTAAATAGTACTC 3'

GeloC-2 (SEQ ID NO: 29)
5' TTTAGGATC<u>GCA</u>ATCGACGAACTTCAAG 3'

GeloC-3-2 (SEQ ID NO: 30)
5' GTTCGTCT<u>GT</u>AAAGATCCTAAATAGTACTCGA 3'

GeloC-4 (SEQ ID NO: 31)
5' GGATCTTT<u>AC</u>AGACGAACTTCAAGAGT 3'

GeloC-5 (SEQ ID NO: 32)
5' TCTTGT<u>GC</u>TTCGTCGATAAAGATCC 3'

GeloC-6 (SEQ ID NO: 33)
5' ATCGACGAAG<u>CA</u>CAAGAGTGCTATTTT 3'

GeloC-9 (SEQ ID NO: 34)
5' GTAAAACCAT<u>GC</u>ATAGCACTCTTGAAGTTCGT 3'

GeloC-10 (SEQ ID NO: 35)
5' AGTGCTAT<u>GC</u>ATGGTTTTACTTGATCAACTGC 3'

GeloC-13 (SEQ ID NO: 36)
5' AGCACA<u>TGT</u>GGTGCCACTTATATTACCTA 3'

GeloC-14 (SEQ ID NO: 37)
5' TAAGTGGCACC<u>ACA</u>TGTGCTAAAGCTCACGGTG 3'

GeloC-15 (SEQ ID NO: 38)
5' TGAC<u>TGT</u>GGACAGTTGGCGGAAATA 3'

GeloC-16 (SEQ ID NO: 39)
5' GCCAACTGTCC<u>ACA</u>GTCATTTGAAAGCGCTACC 3'

GeloC-17 (SEQ ID NO: 40)
5' GATGATCCTGGAAAGGCTTTCGTTTTGGTAGCGCTT 3'

GeloC-18 (SEQ ID NO: 41)
5' AAGCCTTTCCAGGATCATCAGC
TTTTTTGCGCAGCAATGGG 3'

GeloC-19 (SEQ ID NO: 42)
5' AAGCCTTTCCAGGATCATCACAT 3' araB2 (SEQ ID NO: 43)
5' GCGACTCTCTACTGTTTC 3'

HindIII-2 (SEQ ID NO: 44)
5' CGTTAGCAATTTAACTGTGAT 3'

(1) Specifically, a cysteine was introduced at amino acid 247 of gelonin (an aspartic acid which corresponds to the cysteine at position 259 in the ricin A-chain) by PCR with mutagenic primers GeloC-3-2 and GeloC-4 in conjunction with primers HindIII-2 (a primer located in the vector portion of pING3734 or pING3825), Gelo-9 and Gelo-8. Template DNA (pING3734) was amplified with GeloC-3-2 and HindIII-2 and in a concurrent reaction with GeloC-4 and Gelo-9. The products of these reactions were mixed and amplified with the outside primers Gelo-8 and HindIII-2. The reaction product was cut with EcoRI and XhoI, purified, and was inserted into plasmid pING3825 in a three-piece ligation. The DNA sequence of the $Gel_{C247}$ variant was then verified. The plasmid containing the sequence encoding $Gel_{C247}$ was designated pING3737 (A.T.C.C. Accession No. 69009).

(2-3) In the same manner, a cysteine residue was introduced in place of the amino acid at position 248 (a lysine) of gelonin with the mutagenic oligonucleotides GeloC-1 and GeloC-2 to generate analog $Gel_{C248}$ in plasmid pING3741, and a cysteine residue was introduced at amino acid position 239 (a lysine) with primers GeloC-9 and GeloC-10 to generate analog $Gel_{C239}$ in plasmid pING3744.

(4) Also in the same manner, a cysteine residue was introduced at amino acid 244 (a lysine) of gelonin with mutagenic primers GeloC-5 and GeloC-6 to generate analog $Gel_{C244}$ in the plasmid designated pING3736. This variant was prepared by PCR using plasmid pING3734 as template DNA rather than pING3825. It therefore encodes the same N-terminal gelonin amino acid sequence as plasmids pING3737, pING3741, and pING3744, but includes the PCR primer-derived 5'-end 32 nucleotides instead of the native gelonin 5'-end nucleotides.

(5) A cysteine residue was introduced in place of the amino acid (a lysine) at position 10 of gelonin by a similar procedure. A cysteine was introduced with mutagenic primers GeloC-13 and GeloC-14 by amplifying pING3825 with araB2 (a vector primer) and GeloC-14, and in a separate reaction, with GeloC-13 and Gelo-11. These reaction products were mixed and amplified with the outside primers araB2 and Gelo-11. The PCR product was cut with PstI and NcoI, purified, and cloned back into pING3825 to generate analog $Gel_{10}$ in the plasmid designated pING3746 (A.T.C.C. Accession No. 69008).

(6) The asparagine at position 60 of gelonin 10 was replaced with a cysteine residue using two mutagenic oligos, GeloC-15 and GeloC-16, in conjunction with oligos araB2 and Gelo-11 in the same manner as for the $Gel_{C10}$ variant. The plasmid encoding the $Gel_{C60}$ analog was designated pING3749.

(7) Another gelonin variant with a free cysteine residue was generated by replacing one of the two naturally occurring gelonin cysteine residues, the cysteine a position 50, with an alanine. Plasmid pING3824 was amplified with primers GeloC-17 and Gelo-11, and concurrently in a separate reaction with primers GeloC-19 and araB2. The reaction products were mixed and amplified with araB2 and Gelo-11. This product was cut with NcoI and BglII, and cloned back into the vector portion of pING3825 to generate pING3747. This analog was designated $Gel_{44}$ because it contains a cysteine available for disulfide bonding at amino acid position 44.

(8) A gelonin variant in which both the cysteine at position 44 and the cysteine at position 55 of gelonin were changed to alanine residues was constructed by overlap PCR using the mutagenic oligos GeloC-17 and GeloC-18 in conjunction with primers araB2 and Gelo-11. This analog like the native gelonin protein has no cysteine residues available for conjugation. The plasmid encoding the analog was designated pING3750.

(9) The ninth gelonin variant, including alanine residues at positions 44 and 50 and a cysteine residue at position 247, may be generated from plasmids pING3824, pING3750 and pING3737. Plasmid pING3824 is digested with NcoI and XhoI and the vector fragment is isolated. Plasmid pING3750 is cut with NcoI and EcoRI and the 449 bp fragment encoding the portion of gelonin having alanines substituted in the place of cysteines 44 and 50 is isolated. Plasmid pING3737 is cut with EcoRI and XhoI and the 210 bp fragment encoding the portion of gelonin having a cysteine at position 247 is isolated. The three fragments are ligated to generate a gelonin clone including the three amino acid changes.

Each of the eight gelonin variants constructed was transformed into *E. coli* strain E104. Upon induction of bacterial cultures with arabinose, gelonin polypeptide could be detected in the culture supernatants with gelonin-specific antibodies. There were no differences detected in the expression levels of gelonin from plasmids pING3734 and pING3825, or in the levels from any of the gelonin variants. Each protein was produced in *E. coli* at levels approaching 1 g/l.

Reticulocyte Lysate Assay

The ability of gelonin and recombinant gelonin analogs to inhibit protein synthesis in vitro was tested using a reticulocyte lysate assay (RLA) described in Press et al., *Immunol. Letters*, 14, 37–41 (1986). The assay measures the inhibition of protein synthesis in a cell-free system using endogenous globin mRNA from a rabbit red blood cell lysate. Decreased incorporation of tritiated leucine ($^3$H-Leu) was measured as a function of toxin concentration. Serial log dilutions of standard toxin (the 30 kD form of ricin A-chain, abbreviated as RTA 30), native gelonin, recombinant gelonin (rGelonin) and gelonin analogs were tested over a range of 1 μg/ml to 1 pg/ml. Samples were tested in triplicate, prepared on ice, incubated for 30 minutes at 37° C., and then counted on an Inotec Trace 96 cascade ionization counter. By comparison with an uninhibited sample, the picomolar concentration of toxin (pM) which corresponds to 50% inhibition of protein synthesis (IC$_{50}$) was calculated. As is shown in Table 2 below, recombinant gelonin and most of its analogs exhibit activity in the RLA comparable to that of native gelonin. For some of the analogs (such as Gels39), RLA activity was diminished.

TABLE 1

| Toxin | IC$_{50}$ (pM) |
| --- | --- |
| RTA 30 | 2.5 |
| Gelonin | 15 |
| rGelonin | 11 |
| Gel$_{C10}$ | 60 |
| Gel$_{C44}$ | 20 |
| Gel$_{C239}$ | 955 |
| Gel$_{C244}$ | 32 |
| Gel$_{C247}$ | 12 |
| Gel$_{C248}$ | 47 |

Gel$_{C60}$ and the gelonin analog with both native cysteines replaced with alanines were both active in the RLA (data not shown).

Preparation of Gelonin Immunoconjugates

Gelonin analogs of the invention were variously conjugated to murine (A.T.C.C. HB9286) and chimeric H65 antibody and H65 antibody domains (including Fab, Fab' and F(ab')$_2$ fragments) specifically reactive with the human T cell determinant CD5. H65 antibody was prepared and purified according to U.S. patent application Ser. No. 07/306,433, supra. Chimeric H65 antibody was prepared according to methods similar to those described in Robinson et al., *Human Antibodies and Hybridomas*, 2, 84–93 (1991).

(1) Conjugation to H65 antibodies

To expose a reactive sulfhydryl, the unpaired cysteine residues of the gelonin analogs were first reduced by incubation with 0.1 to 2 mM DTT (30–60 minutes at room temperature), and then were desalted by size-exclusion chromatography.

Specifically, the Gel$_{C248}$ analog (3.8 mg/ml) was treated with 2 mM DTT for 60 minutes in 0.1 M NaPhosphate, 0.25 M NaCl, pH 7.5 buffer. The Gel$_{C244}$ variant (7.6 mg/ml) was treated with 2 mM DTT for 30 minutes in 0.1 M NaPhosphate, 0.25 M NaCl, pH 7.5 buffer. The Gel$_{C247}$ analog (4 mg/ml) was treated with 2 mM DTT for 30 minutes in 0.1 M NaPhosphate, 0.5 M NaCl, pH 7.5 buffer with 0.5 mM EDTA. The Gel$_{C239}$ variant (3.2 mg/ml) was treated with 2 mM DTT for 30 minutes in 0.1 m NaPhosphate, 0.5 M NaCl, pH 7.5 buffer with 0.5 mM EDTA. The Gel$_{C44}$ analog (4.2 mg/ml) was treated with 0.1 mM DTT for 30 minutes in 0.1 M NaPhosphate, 0.1 M NaCl, pH 7.5 buffer with 0.5 mM EDTA. Lastly, the Gel$_{C10}$ variant (3.1 mg/ml) was treated with 1 mM DTT for 20 minutes in 0.1 M NaPhosphate, 0.1 M NaCl, pH 7.5 buffer with 1 mM EDTA.

The presence of a free sulfhydryl was verified by reaction with DTNB and the average value obtained was 1.4±0.65 SH/molecule. No free thiols were detected in the absence of reduction.

H65 antibody and chimeric H65 antibody was chemically modified with the hindered linker 5-methyl-2-iminothiolane (M2IT) at lysine residues to introduce a reactive sulfhydryl group as described in Goff et al., *Bioconjugate Chem.*, 1, 381–386 (1990).

Specifically, for conjugation with Gel$_{C248}$ and Gel$_{C244}$, murine H65 antibody at 4 mg/mL was derivitized with 18x M2IT and 2.5 mM DTNB in 25 mM TEOA, 150 mM NaCl, pH 8 buffer for 1 hour at 23° C. The reaction gave 1.9 linkers per antibody as determined by DTNB assay.

For conjugation with Gel$_{C247}$ and Gel$_{C239}$, H65 antibody at 4.7 mg/mL was derivitized with 20x M2IT and 2.5 mM DTNB in 25 mM TEOA 150 mM NaCl, pH 8 buffer for 50 minutes at 23° C. The reaction gave 1.6 linkers per antibody as determined by DTNB assay.

Before reaction with Gel$_{C44}$, H65 antibody at 5.8 mg/mL was derivitized with 20x m2IT and 2.5 mM DTNB in 25 mM TEOA, 150 mM NaCl, pH 8 buffer for 30 minutes at 23° C. The reaction gave 1.5 linkers per antibody as determined by DTNB assay.

For conjugation with Gel$_{C10}$, H65 antibody at 2.2 mg/mL was derivitized with 10x m2IT and 2.5 mM DTNB in 25 mM TEOA, 150 mM NaCl, pH 8 buffer for 1 hour at 23° C. The reaction gave 1.4 linkers per antibody as determined by DTNB assay.

Chimeric H65 antibody was prepared for conjugation in a similar manner to murine H65 antibody.

Two methods were initially compared for their effectiveness in preparing immunoconjugates with recombinant gelonin. First, the native disulfide bond in recombinant gelonin was reduced by the addition of 2 mM DTT at room temperature for 30 minutes. The reduced gelonin was recovered by size-exclusion chromatography on a column of Sephadex GF-05LS and assayed for the presence of free sulfhydryls by the DTNB assay. 1.4 free SH groups were detected. This reduced gelonin was then reacted with H65-(M2IT)-S-S-TNB (1.8 TNB groups/H65). Under these experimental conditions, little or no conjugate was prepared between reduced gelonin and thiol-activated H65 antibody.

In contrast, when both the recombinant gelonin and the H65 antibody were first derivitized with the cross-linker M2IT (creating gelonin-(M2IT)-SH and H65-(M2IT)-S-S-TNB) and then mixed together, H65-(M2IT)-S-S-(M2IT)-gelonin conjugate was prepared in good yield (toxin/antibody ratio of 1.6). The starting materials for this conjugation (gelonin-(M2IT)-SH and H65-(M2IT)-S-S-TNB) contained linker/protein ratios of 1.2 and 1.4, respectively.

The reduced gelonin analogs were mixed with H65-(M2IT)-S-S-TNB to allow conjugation. The following conjugation reactions were set up for each analog: 23 mg (in 7.2 ml) of H65-M2IT-TNB were mixed with a 5-fold molar excess of Gels4$_5$ (23 mg in 6 ml) for 2 hours at room temperature, then for 18 hours overnight at 4° C.; 23 mg (in 7.3 ml) of H65-m2IT-TNB were mixed with a 5fold molar excess of Gel$_{C244}$ (23 mg in 3 ml) for 3 hours at room temperature, then for 18 hours overnight at 4° C.; 9 mg (in 2.8 mL) of H65-m2IT-TNB were mixed with a 5-fold molar excess of Gel$_{C247}$ (9 mg in 2.25 mL) for 2 hours at room temperature, then for 5 nights at 4° C.; 9 mg (in 2.8 mL) of H65-m2IT-TNB were mixed with a 5-fold molar excess of Gels39 (9 mg in 2.6 mL) for 2 hours at room temperature, then at 4° C. for 3 days; 12 mg (in 1.9 mL) of H65-m2IT-TNB were mixed with a 5.6-fold molar excess of Gel$_{C44}$ (13.44 mg in 3.2 mL) for 4.5 hours at room temperature, then 4° C. overnight; and 11 mg of H65-m2IT-TNB were mixed with a 5-fold molar excess of Gel$_{C10}$ (11 mg in 3.5 mL) for 4 hours at room temperature, then at 4° C. overnight.

Following conjugation, unreacted M2IT linkers on the antibody were quenched with 1:1 mole cysteamine to linker for 15 minutes at room temperature. The quenched reaction solution was then loaded onto a gel filtration column [Sephadex G-150 (Pharmacia) in the case of Gel$_{C248}$, Gel$_{C247}$, Gel$_{C244}$ and Gel$_{239}$ and an AcA-44 column (IBF Biotecnics, France) in the case of Gel$_{C44}$ and Gel$_{C10}$]. The reactions were run over the gel filtration columns and eluted with 10 mM Tris, 0.15M NaCl pH 7. The first peak off each column was loaded onto Blue Toyopearl ®resin (TosoHaas, Philadelphia, Pa.) in 10 mM Tris, 30 mM NaCl, pH 7 and the product was eluted with 10 mM Tris, 0.5 M NaCl, pH 7.5.

Samples of the final conjugation products were run on 5% non-reduced SDS PAGE, Coomassie stained and scanned with a Shimadzu laser densitometer to quantitate the number of toxins per antibody (T/A ratio). The yield of final product for each analog conjugate was as follows: Gel$_{C248}$, 17 mg with a T/A ration of 1.6; Gel$_{C247}$, 1.1 mg with a T/A ratio of 1; Gel$_{C244}$, 4.5 mgs with a T/A ratio of 1.46; Gel$_{C239}$, 2.9 mg with a T/A ratio of 2.4; Gel$_{C44}$, 7.3 mg with a T/A ratio of 1.22; and Gel$_{C10}$, 6.2 mg with a T/A ratio of 1.37. Conjugation efficiency (i.e., conversion of free antibody to immunoconjugate) was significantly greater (~80%) for some analogs (Gel$_{C10}$, Gel$_{C44}$, Gel$_{C239}$, Gel$_{C247}$, and Gel$_{C248}$) than for others (~10%, Gel$_{C244}$).

Control immunoconjugates of H65 antibody and chimeric H65 antibody with native and recombinant gelonin were prepared by similar procedures.

(2) Conjugation with antibody fragments

Analog Gel$_{C247}$ was conjugated to various chimeric [cFab, cFab' and cF(ab')$_2$] and "human engineered" [heI Fab, heI Fab' and heI F(ab')$_2$] antibody fragments. Chimeric H65 antibody fragments may be prepared according to the methods described in U.S. patent application Ser. No. 07/714,175, supra. H65 variable regions used to encode the variable regions of H65 antibody fragments were human engineered (referring to the replacement of selected murine-encoded amino acids to make the H65 antibody sequences less immunogenic to humans) according to the methods described in co-pending, co-owned U.S. patent application Ser. No. 07/808,454, now abandoned filed Dec. 13, 1991, which is incorporated by reference herein.

The H65 antibody fragments were conjugated to Gel$_{C247}$ analog basically as described below for conjugation of human engineered Fab and Fab' fragments to Gel$_{C247}$.

The heI Fab was dialyzed into 25 mM TEOA buffer, 250 mM NaCl, pH 8 and then concentrated to 6.8 mg/mL prior to derivitization with the M2IT crosslinker. For the linker reaction, M2IT was used at 20-fold molar excess, in the presence of 2.5 mM DTNB. The reaction was allowed to proceed for 30 minutes at room temperature, then desalted on GF05 (gel filtration resin) and equilibrated in 0.1 M Na Phosphate, 0.2M NaCl, pH 7.5. A linker number of 1.8 linkers per Fab was calculated based on the DTNB assay. The heI Fab-M2IT-TNB was concentrated to 3.7 mg/mL prior to conjugation with Gel$_{C247}$.

Gel$_{C247}$ at 12.8 mg/mL in 10 mM Na Phosphate, 0.3M NaCl, was treated with 1 mM DTT, 0.5 mM EDTA for 20 minutes at room temperature to expose a reactive sulfhydryl for conjugation and then was desalted on GF05 and equilibrated in 0.1 M Na Phosphate, 0.2 M NaCl, pH 7.5. Free thiol content was determined to be 0.74 moles of free SH per mole of Gel$_{C247}$ using the DTNB assay. The gelonin was concentrated to 8.3 mg/mL prior to conjugation with activated antibody.

The conjugation reaction between the free thiol on GelS47 and the derivitized heI Fab-M2IT-TNB, conditions were as follows. A 5-fold excess of the gelonin analog was added to activated heI Fab-M2IT-TNB (both proteins were in 0.1M Na Phosphate, 0.2M NaCl, pH 7.5) and the reaction mixture was incubated for 3.5 hours at room temperature and then overnight at 4° C. Following conjugation, untreated M2IT linkers were quenched with 1:1 mole cysteamine to linker for 15 minutes at room temperature. The quenched reaction solution was loaded onto a gel filtration column (G-75) equilibrated with 10 mM Tris, 150 mM NaCl, pH 7. The first peak off this column was diluted to 30 mM NaCl with 10 mM Tris, pH7 and loaded on Blue Toyopearl ®. The product was eluted with 10 mM Tris, 0.5 M NaCl, pH 7.5.

Similarly, the H65 heI Fab' fragment was dialyzed into 25 mM TEOA buffer, 400 mM NaCl, pH 8 at 2.9 mg/mL prior to derivitization with the M2IT crosslinker. For the linker reaction, M2IT was used at 20-fold molar excess, in the presence of 2.5 mM DTNB. The reaction was allowed to proceed for 1 hour at room temperature then it was desalted on GF05 (gel filtration resin) and equilibrated in 0.1 M Na Phosphate, 0.2 M NaCl, pH 7.5. A linker number of 1.6 linkers per Fab' was calculated based on the DTNB assay. The heI Fab'-M2IT-TNB was concentrated to 3.7 mg/mL prior to conjugation with Gel$_{C247}$.

The Gel$_{C247}$ at 77 mg/mL was diluted with in 10 mM Na Phosphate, 0.1 M NaCl to a concentration of 5 mg/mL, treated with 1 mM DTT, 0.5 mM EDTA for 30 minutes at room temperature to expose a free thiol for conjugation and then was desalted on GF05 and equilibrated in 0.1 M Na Phosphate, 0.2 M NaCl, pH 7.5. Free thiol content was determined to be 1.48 moles of free SH per mole of Gel$_{C247}$ using the DTNB assay. The Gel$_{C247}$ was concentrated to 10 mg/mL prior to conjugation with activated heI Fab'-M2IT-TNB.

For the reaction between the free thiol on Gel$_{C247}$ and the derivitized heI Fab'-M2IT-TNB, conditions were as follows. A 5.7-fold molar excess of gelonin was added to activated heI Fab'-M2IT-TNB and the final salt concentration was adjusted to 0.25 M. The reaction mix was incubated for 1.5 hours at room temperature and then over the weekend at 4° C. Following conjugation, unreacted M2IT linkers were quenched with 1:1 mole cysteamine to linker for 15 minutes at room temperature. The quenched reaction solution was loaded onto a gel filtration column (AcA54) equilibrated with 10 mM Tris, 250 mM NaCl, pH 7.5. The first peak off this column was diluted to 20 mM NaCl with 10 mM Tris, pH 7 and loaded on Blue Toyopearl ® which was equilibrated in 10 mM Tris, 20 mM NaCl, pH 7. The column was then washed with 10 mM Tris, 30 mM Nacl, pH 7.5. The product was eluted with 10 mM Tris, 1 M NaCl, pH 7.5.

Whole Cell Kill Assays

Immunoconjugates prepared with gelonin and gelonin analogs were tested for cytotoxicity against an acute lymphoblastoid leukemia T cell line (HSB2 cells) and against human peripheral blood mononuclear cells (PBMCs). Immunoconjugates of ricin A-chain with H65 antibody (H65-RTA) and antibody fragments were also tested. The ricin A-chain (RTA) as well as the H65-RTA immunoconjugates were prepared and purified according to U.S. patent application Ser. No. 07/306,433, supra.

Briefly, HSB2 cells were incubated with immunotoxin and the inhibition of protein synthesis in the presence of immunotoxin was measured relative to untreated control cells. The standard immunoconjugates H65-RTA (H65 derivatized with SPDP linked to RTA), H65-Gelonin and H65-rGelonin, H65 fragment immunoconjugate, and gelonin immunoconjugate samples were diluted with RPMI without leucine at half-log concentrations ranging from 2000 to 0.632 ng/ml. All dilutions were added in triplicate to microtiter plates containing $1 \times 10^5$ HSB2 cells. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar concentration (pM) of immunotoxin which resulted in a 50% inhibition of protein synthesis (IC$_{50}$) was calculated. In order to normalize for conjugates containing differing amounts of toxin or toxin analog, the cytotoxicity data were converted to picomolar toxin (pM T) by multiplying the conjugate IC$_{50}$ (in pM) by the toxin/antibody ratio which is unique to each conjugate preparation.

The PMBC assays were performed as described by Fishwild et al., *Clin. and Exp. Immunol.*, 86, 506–513 (1991) and involved the incubation of immunoconjugates with PBMCs for a total of 90 hours. During the final 16 hours of incubation, $^3$H-thymidine was added; upon completion, immunoconjugate-induced inhibition of DNA synthesis was quantified. The activities of the H65 and chimeric H65 antibody conjugates against HSB2 cells and PBMC cells are listed in Table 2 below.

TABLE 2

| Conjugate | IC$_{50}$ (pM T) | |
|---|---|---|
| | HSB2 Cells | PBMCs |
| H65-RTA | 143 | 459 |
| H65-(M2IT)-S-S-(M2IT)-Gelonin | 1770 | 81 |
| H65-(M2IT)-S-S-(M2IT)-rGelonin | 276 | 75 |
| H65-(M2IT)-S-S-Gel$_{C10}$ | 140 | 28 |
| H65-(M2IT)-S-S-Gel$_{C44}$ | 99 | 51 |
| H65-(M2IT)-S-S-Gel$_{C239}$ | 2328 | 180 |
| H65-(M2IT)-S-S-Gel$_{C244}$ | >5000 | >2700 |
| H65-(M2IT)-S-S-Gel$_{C247}$ | 41 | 35 |
| H65-(M2IT)-S-S-Gel$_{C248}$ | 440 | 203 |
| cH65-RTA$_{30}$ | 60 | 400 |
| cH65-(M2IT)-S-S-(M2IT)-Gelonin | 1770 | 140 |
| cH65-(M2IT)-S-S-(M2IT)-rGelonin | 153 | 120 |
| cH65-(M2IT)-S-S-Gel$_{C239}$ | >7000 | 290 |
| cH65-(M2IT)-S-S-Gel$_{C247}$ | 34 | 60 |
| cH65-(M2IT)-S-S-Gel$_{C248}$ | 238 | 860 |

Against HSB2 cells, many of the gelonin analog immunoconjugates were significantly more potent than conjugates prepared with native gelonin or recombinant, unmodified gelonin, both in terms of a low IC$_{50}$ value, but also in terms of a greater extent of cell kill. Against human PBMCs, the gelonin analog conjugates were at least as active as native and recombinant gelonin. Importantly, however, some of the conjugates (such as Gel$_{C10}$Gel$_{C10}$, and Gel$_{C247}$) exhibited an enhanced potency against PBMCs, and also exhibited an enhanced level of cell kill (data not shown).

The activities of the H65 antibody fragment conjugates against HSB2 cells and PBMC cells are listed in Tables 3 and 4 below, wherein extent of kill in Table 4 refers to the percentage of protein synthesis inhibited in HSB2 cells at the highest immunotoxin concentration tested (1 μg/ml).

TABLE 3

| Conjugate | IC$_{50}$ (pM T) | |
|---|---|---|
| | HSB2 Cells | PBMCs |
| cFab'-RTA 30 | 530 | 1800 |
| cFab'-rGelonin | 135 | 160 |
| cFab'-Gel$_{C247}$ | 48 | 64 |
| cF(ab')$_2$-RTA 30 | 33 | 57 |
| cF(ab')$_2$-rGelonin | 55 | 34 |
| cF(ab')$_2$-Gel$_{C247}$ | 23 | 20 |
| cF(ab')$_2$-Gel$_{C248}$ | 181 | 95 |

TABLE 4

| Conjugate | IC$_{50}$ (pM T) | |
|---|---|---|
| | HSB2 Cells | Extent of Kill |
| he1 Fab'-Gel$_{C247}$ | 57.7 | 93% |
| he1 Fab-Gel$_{247}$ | 180 | 94% |
| cFab'-Gel$_{C247}$ | 47.5 | 93% |
| cF(ab')$_2$-rGelonin | 45.4 | 85% |
| mF(ab')$_2$-Gel$_{C247}$ | 77.5 | 83% |
| cF(ab')$_2$-Gel$_{C247}$ | 23.2 | 85% |

The cFab'-Gel$_{247}$ immunoconjugate is clearly more cytotoxic than cFab' conjugates with recombinant gelonin or RTA 30.

Solubility

Gelonin analogs and gelonin immunoconjugates exhibited enhanced solubility in comparison to recombinant gelonin, native RTA 30 and immunoconjugates of recombinant gelonin and RTA 30.

Disulfide Bond Stability Assay

The stability of the disulfide bond linking a RIP to a targeting molecule (such as an antibody) is known to influence the lifespan of immunoconjugates in vivo [see Thorpe et al., *Cancer Res.*, 47, 5924–5931 (1987)]. For example, conjugates in which the disulfide bond is easily broken by reduction are less stable and less efficacous in animal models [see Thorpe et al., *Cancer Res.*, 48, 6396–6403 (1988)].

Immunoconjugates prepared with native gelonin, recombinant gelonin and gelonin analogs were therefore examined in an in vitro disulfide bond stability assay similar to that described in Wawrzynczak et al., *Cancer Res.*, 50, 7519–7526 (1990). Conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparison with the amount of RIP released by high concentrations of 2-mercaptoethanol (to determine 100% release), the concentration of glutathione required to release 50% of the RIP (the RC$_{50}$) was calculated. The results of assays for H65 antibody conjugates are set out in Table 5 below, wherein multiple RC$_{50}$ results or ranges given for a

TABLE 5

| Conjugate | RC$_{50}$ (mM) |
|---|---|
| H65-RTA 30 | 3.2 |

TABLE 5-continued

| Conjugate | RC$_{50}$ (mM) |
|---|---|
| H65-(M2IT)-S-S-(M2IT)-gelonin | 11.1 |
| H65-(M2IT)-S-S-(M2IT)-rGelonin | 3.0 |
| H65-(M2IT)-S-S-Gel$_{C10}$ | 2.5 |
| H65-(M2IT)-S-S-Gel$_{C44}$ | 0.6 |
| H65-(M2IT)-S-S-Gel$_{C239}$ | 774.0 |
| H65-(M2IT)-S-S-Gel$_{C244}$ | 1.2 |
| H65-(M2IT)-S-S-Gel$_{C247}$ | 0.1 |
| H65-(M2IT)-S-S-Gel$_{C248}$ | 0.4 |
| cH65-RTA 30 | 2.50 |
| cH65-(M2IT)-S-S-(M2IT)-rGelonin | 2.39 |
| cH65-(M2IT)-S-S-Gel$_{C247}$ | 0.11 |
| cH65-(M2IT)-S-S-Gel$_{C248}$ | 0.32 |

The foregoing results indicate that the stability of the bonds between the different gelonin proteins and H65 antibody varied greatly. With the exception of Gel$_{C10}$ and Gel$_{C239}$, most of the gelonin analogs resulted in conjugates with linkages that were somewhat less stable in this in vitro assay than the dual-linker chemical conjugate. The stability of the Gel$_{C239}$ analog, however, was particularly enhanced.

The results of the assay for H65 antibody fragment conjugates are set out in Table 6 below.

TABLE 6

| Conjugate | RC$_{50}$ (mM) |
|---|---|
| he1 Fab'-Gel$_{C247}$ | 0.07 |
| cFab'-Gelonin | 1.27 |
| cFab'-Gel$_{C247}$ | 0.08 |
| cF(ab')$_2$-RTA 30 | 3.69 |
| cF(ab')$_2$-rGelonin | 2.30 |
| cF(ab')$_2$-Gel$_{C247}$ | 0.09 |
| cF(ab')$_2$-Gel$_{C248}$ | 0.32 |

From the RC$_{50}$ results presented in Tables 5 and 6, it appears that the particular RIP analog component of each immunotoxin dictates the stability of the immunotoxin disulfide bond in vitro.

Example 2

BRIP possesses characteristics which make it an attractive candidate for a component of immunotoxins. BRIP is a naturally unglycosylated protein that may have reduced uptake in the liver and enhanced circulatory residence time in vivo. Additionally, BRIP is less toxic and less immunogenic in animals than the A-chain of ricin. Cloning of the BRIP gene and expression of recombinant BRIP in an E. coli expression system obviates the need to purify native BRIP directly from barley, and enables the development of analogs of BRIP which may be conjugated with an available cysteine residue for conjugation to antibodies.

Purification of BRIP and Generation of Polyclonal Antibodies to BRIP

Native BRIP was purified from pearled barley flour. Four kilograms of flour was extracted with 16 liters of extraction buffer (10 mM NAPO4, 25 mM NaCl, pH 7.2) for 20 hours at 4° C. The sediment was removed by centrifugation, and 200 ml of packed S-Sepharose (Pharmacia, Piscataway, N.J.) was added to absorb BRIP. After mixing for 20 hours at 4° C., the resin was allowed to settle out, rinsed several times with extraction buffer and then packed into a 2.6×40 cm column. Once packed, the column was washed with extraction buffer (150 ml/h) until the absorbance of the effluent approached zero. BRIP was then eluted with a linear gradient of 0.025 to 0.3 M NaCl in extraction buffer and 5 ml fractions were collected. BRIP-containing peaks (identified by Western analysis of column fractions) were pooled, concentrated to about 20 ml, and then chromatographed on a 2.6×100 cm Sephacryl S-200HR (Pharmacia) column equilibrated in 10 mM NaPO4, 125 mM NaCl, pH 7.4 (10 ml/hr). BRIP-containing peaks were pooled again, concentrated, and stored at −70° C.

The resulting purified BRIP protein had a molecular weight of about 30,000 Daltons, based upon the mobility of Coomassie-stained protein bands following SDS-PAGE. The amino acid composition was consistent with that published by Asano et al., *Carlsberg Res. Comm.*, 49, 619–626 (1984).

Rabbits were immunized with purified BRIP to generate polyclonal antisera.

Cloning of the BRIP Gene

A cDNA expression library prepared from germinating barley seeds in the phage λ expression vector λZAPII was purchased from Stratagene, La Jolla, Calif. Approximately 700,000 phage plaques were screened with anti-BRIP polyclonal antisera and 6 immunoreactive plaques were identified. One plaque was chosen, and the cDNA contained therein was excised from λZAPII with EcoRI and subcloned into pUC18 generating the vector pBS1. The cDNA insert was sequenced with Sequenase (United States Biochemical, Cleveland, Ohio). The DNA sequence of the native BRIP gene is set out in SEQ ID NO: 12 and in FIG. 11. To confirm that cDNA encoded the native BRIP gene, the cDNA was expressed in the E. coli plasmid pKK233-2 (Pharmacia). BRIP protein was detected in IPTG-induced cells transformed with the plasmid by Western analysis with above-described rabbit anti-BRIP antisera.

Construction of an E. coli Expression Vector Containing the BRIP Gene

Barley cDNA containing the BRIP gene was linked to a pelB leader sequence and placed under control of an araB promoter in a bacterial secretion vector.

An intermediate vector containing the BRIP gene linked to the pelB leader sequence was generated. Plasmid pBS1 was cut with NcoI, treated with Mung Bean Nuclease, cut with BamHI and the 760 bp fragment corresponding to amino acids 1–256 of BRIP was purified from an agarose gel. Concurrently, a unique XhoI site was introduced downstream of the 3'-end of the BRIP gene in pBS1 by PCR amplification with a pUC18 vector primer (identical to the Reverse® primer sold by NEB or BRL but synthesized on a Cyclone Model 8400 DNA synthesizer) and the specific primer BRIP 3'Xho. The sequence of each of the primers is set out below.

Reverse (SEQ ID NO: 45)
5' AACAGCTATGACCATG 3'

BRIP 3'Xho (SEQ ID NO: 46)
5' TGAACTCGAGGAAAACTACCTATTTCCCAC 3'

Primer BRIP 3'Xho includes a portion corresponding to the last 8 bp of the BRIP gene, the termination codon and several base pairs downstream of the BRIP gene, and an additional portion that introduces a XhoI site in the resulting PCR fragment. The PCR reaction product was digested with BamHI and XhoI, and an 87 bp fragment containing the 3'-end of the BRIP gene was purified on a 5% acrylamide gel. The 760 and 87 bp purified BRIP fragments were ligated in the vector pING1500 adjacent to the PelB leader sequence. pING1500 had previously been cut with SstI, treated with T4 polymerase, cut with XhoI, and purified. The DNA sequence at the junction of the pelB leader and the 5'-end of the BRIP gene was verified by DNA sequence analysis. This vector was denoted pING3321-1.

The final expression vector was assembled by placing the BRIP gene under the control of the inducible araB promoter. Plasmid pING3321-1 was cut with PstI and XhoI, and the BRIP gene linked to the pelB leader was purified from an agarose gel. The expression vector pING3217, containing the araB promoter, was cut with PstI and XhoI and ligated to the BRIP gene. The expression vector was denoted pING3322.

Arabinose induction of *E. coli* cells containing the plasmid pING3322 in a fermenter resulted in the production of about 100 mg per liter of recombinant BRIP. *E. coli*-produced BRIP displays properties identical to BRIP purified directly from barley seeds.

Construction of BRIP Analogs With a Free Cysteine Residue

The BRIP protein contains no cysteine residues, and therefore contains no residues directly available which may form a disulfide linkage to antibodies or other proteins. Analogs of recombinant BRIP were generated which contain a free cysteine residue near the C-terminus of the protein. Three residues of the BRIP protein were targets for amino acid substitutions. Comparison of the amino acid sequence of BRIP to the known tertiary structure of the ricin A-chain (see FIG. 2) suggested that the three positions would be available near the surface of the molecule. The three BRIP analogs include cysteines substituted in place of serine$_{277}$, alanine$_{270}$, and leucine$_{256}$ of the native protein, and were designated BRIP$_{C277}$, BRIP$_{C270}$ and BRIP$_{C256}$, respectively.

(1) A plasmid vector capable of expressing the BRIP$_{C277}$ analog was constructed by replacing the 3'-end of the BRIP gene with a DNA segment conferring the amino acid change. The EcoRI fragment containing the BRIP gene from pBS1 was subcloned into M13mp18, and single-stranded DNA (anti-sense strand) was amplified by PCR with primers OBM2 (corresponding nucleotides -11 to +8 of the BRIP gene) and OMB4 (corresponding to amino acids 264–280 of BRIP and the termination codon of BRIP, and incorporating the substitution of a cysteine codon for the native codon for serine$_{277}$ of native BRIP). The sequences of primers OBM2 and OMB4, wherein the underlined nucleotides encode the substituted cysteine, are set out below.

OBM2 (SEQ ID NO: 47)
5' GCATTACATCCATGGCGGC 3'

OMB4 (SEQ ID NO: 48)
5' GATATCTCGAGTTAACTATTTCCCACC<u>ACA</u>CG
CATGGAACAGCTCCAGCGCCTTGGCCACCGTC 3'

A fragment containing a BRIP gene in which the codon for the amino acid at position 277 was changed to a cysteine codon was amplified. The fragment was cloned into the SmaI site of pUC19 (BRL) and the plasmid generated was denoted pMB22. pMB22 was digested with EcoRI and an EcoRI-XhoI linker (Clonetech, Palo Alto, Calif.) was ligated into the vector. Subsequent digestion with XhoI and religation generated vector pINGMB2X. A BamHI to XhoI fragment encoding the 3'-end of BRIP with the altered amino acid was excised from pMB2X and the fragment was purified on a 5% acrylamide gel. This fragment along with an EcoRI to BamHI fragment containing the pelB leader sequence and sequences encoding the first 256 amino acids of BRIP were substituted in a three piece ligation into pING3322 cut with EcoRI and XhoI. The resulting vector containing the BRIP$_{C277}$ analog was designated. pING3803 (A.T.C.C. Accession No. 68722).

(2) A BRIP analog with a free cysteine at position 256 was constructed using PCR to introduce the amino acid substitution. A portion of the expression plasmid pING3322 was amplified with primers BRIP-256 and HindIII-2. The sequence of each primer is set out below.

BRIP-256 (SEQ ID NO: 49)
5' TG<u>TC</u>TGTTCGTGGAGGTGCCG 3'

HindIII-2 (SEQ ID NO: 50)
5' CGTTAGCAATTTAACTGTGAT 3'

Nucleotides 4–21 of primer BRIP-256 encode amino acids 256–262 of BRIP while the underlined nucleotides specify the cysteine to be substituted for the leucine at the corresponding position of the native BRIP protein. Primer HindIII-2 corresponds to a portion of the plasmid. The PCR product, which encodes the carboxyl terminal portion of the BRIP analog, was treated with T4 polymerase, cut with XhoI, and the resulting fragment was purified on a 5% acrylamide gel. Concurrently, plasmid pING3322 was cut with BamHI, treated with T4 polymerase, cut with EcoRI, and the fragment containing the pelB leader sequence and sequences encoding the first 256 amino acids of BRIP was purified. The two fragments were then assembled back into pING3322 to generate the gene encoding the analog BRIP$_{C256}$. This plasmid is denoted pING3801.

(3) A BRIP analog with a cysteine at position 270 was also generated using PCR. A portion of the expression plasmid pING3322 was amplified with primers BRIP-270 and the HindIII-2 primer (SEQ ID NO: 50). The sequence of primer BRIP-270 is set out below.

BRIP-270 (SEQ ID NO: 51)
5' CCAAGTGTCTGGAGCTGTTCCATGCGA 3'

Primer BRIP-270 corresponds to amino acids 268–276 of BRIP with the exception of residue 270. The codon of the primer corresponding to position 270 specifies a cysteine instead of the alanine present in the corresponding position in native BRIP. The PCR product was treated with T4 polymerase, cut with XhoI, and the 51 bp fragment, which encodes the carboxyl terminal portion of the analog, was purified on a 5% acrylamide gel. The fragment (corresponding to amino acids 268–276 of BRIP$_{C270}$) was cloned in a three piece ligation along with the internal 151 bp BRIP restriction fragment from SstII to MscI (corresponding to BRIP amino acids 217–267) from plasmid pING3322, and restriction fragment from SstII to XhoI from pING3322 containing the remainder of the BRIP gene. The plasmid generated contains the gene encoding the BRIP$_{C270}$ analog and is designated pING3802.

Purification of Recombinant BRIP and the BRIP Analogs

Recombinant BRIP (rBRIP) and the BRIP analogs with free cysteine residues were purified essentially as described for native BRIP except they were prepared from concentrated fermentation broths. For rBRIP, concentrated broth from a 10 liter fermentation batch was exchanged into 10 mM Tris, 20 mM NaCl pH 7.5, loaded onto a Sephacryl S-200 column, and eluted with a 20 to 500 mM NaCl linear gradient. Pooled rBRIP was further purified on a Blue Toyopearl ® column (TosoHaas) loaded in 20 mM NaCl and eluted in a 20 to 500 mM NaCl gradient in 10mM Tris, pH 7.5. For BRIP analogs, concentrated fermentation broths were loaded onto a CM52 column (Whatman) in 10 mM phosphate buffer, pH 7.5, and eluted with a 0 to 0.3M NaCl linear gradient. Further purification was by chromatography on a Blue Toyopearl ® column.

Reticulocyte Lysate Assay

The ability of the rBRIP and the BRIP analogs to inhibit protein synthesis in vitro was tested by reticulocyte lysate assay as described in Example 1. Serial log dilutions of standard toxin (RTA 30), native BRIP, rBRIP and BRIP analogs were tested over a range of 1 μg/ml to 1 pg/ml. By comparison with an uninhibited sample, the picomolar concentration of toxin (pM) which corresponds to 50% inhibition of protein synthesis ($IC_{50}$) was calculated. The results of the assays are presented below in Table 7.

TABLE 7

| Toxin | $IC_{50}$ (pM) |
| --- | --- |
| RTA 30 | 3.1 |
| Native BRIP | 15 |
| rBRIP | 18 |
| $BRIP_{C256}$ | 23 |
| $BRIP_{C270}$ | 20 |
| $BRIP_{C277}$ | 24 |

The RLA results indicate that the BRIP analogs exhibit ribosome-inactivating activity comparable to that of the recombinant and native BRIP toxin. All the analogs retained the natural ability of native BRIP to inhibit protein synthesis, suggesting that amino acid substitution at these positions does not affect protein folding and activity.

Construction of BRIP Immunoconjugates

Immunoconjugates of native BRIP with 4A2 (described in Morishima et al., *J. Immunol.*, 129, 1091 (1982) and H65 antibody (obtained from hybridoma A.T.C.C. HB9286) which recognize the T-cell determinants CD7 and CD5, respectively, were constructed. Immunoconjugates of ricin A-chains (RTAs) with 4A2 and H65 antibody were constructed as controls. The H65 antibody and ricin A-chains as well as the RTA immunoconjugates were prepared and purified according to U.S. patent application Ser. No. 08/130,406 supra.

To prepare immunoconjugates of native BRIP, both the antibody (4A2 or H65) and native BRIP were chemically modified with the hindered linker 5-methyl-2-iminothiolane (M2IT) at lysine residues to introduce a reactive sulfhydryl group as described in Goff et al., *Bioconjugate Chem.*, 1, 381–386 (1990). BRIP (3 mg/ml) was first incubated with 0.5 mM M2IT and 1 mM DTNB in 25 mM triethanolamine, 150 mM NaCl, pH 8.0, for 3 hours at 25° C. The derivatized BRIP-(M2IT)-S-S-TNB was then desalted on a column of Sephadex GF-05LS and the number of thiol groups introduced was quantitated by the addition of 0.1 mM DTT. On average, each BRIP molecule contained 0.7 SH/mol.

4A2 or H65 antibody (4 mg/ml) in triethanolamine buffer was similarly incubated with M2IT (0.3 mM) and DTNB (1 mM) for 3 hours at 25° C. Antibody-(M2IT)-S-S-TNB was then desalted and the TNB:antibody ratio was determined. To prepare the conjugate, the BRIP-(M2IT)-S-S-TNB was first reduced to BRIP-(M2IT)-SH by treatment with 0.5 mM DTT for 1 hour at 25° C., desalted by gel filtration of Sephadex® GF-05LS to remove the reducing agent, and then mixed with antibody-(M2IT)-S-S-TNB.

Following a 3 hour incubation at 25° C., and an additional 18 hours at 4° C., the conjugate was purified by sequential chromatography on AcA44 (IBF) and Blue Toyopearl®. Samples of the final product were run on 5% non-reducing SDS PAGE, Coomassie stained, and scanned with a Shimadzu laser densitometer to quantitate the number of toxins per antibody.

The BRIP analogs containing a free cysteine were also conjugated to 4A2 and H65 antibodies. The analogs were treated with 50 mM DTT either for 2 hours at 25° C. or for 18 hours at 4° C. to expose the reactive sulfhydryl group of the cysteine and desalted. The presence of a free sulfhydryl was verified by reaction with DTNB [Ellman et al., *Arch. Biochem. Biophys*, 82, 70–77 (1959)]. 4A2 or H65 antibody derivatized as described above with M2IT was incubated with the reduced BRIP analogs at a ratio of 1:5 at room temperature for 3 hours and then overnight at 4° C. Immunoconjugates H65-$BRIP_{C256}$, 4A2-$BRIP_{C256}$, H65-$BRIP_{C277}$ were prepared in 25 mM triethanolamine, 150 mM NaCl pH 8, while immunoconjugates H65-$BRIP_{C270}$, 4A2-$BRIP_{C270}$ and 4A2-$BRIP_{C277}$ were prepared in 0.1 M sodium phosphate, 150 mM NaCl pH 7.5. Following conjugation, 10 μM mercaptoethylamine was added for 15 minutes at 25° C. to quenched any unreacted m2IT linkers on the antibody. The quenched reaction solution was promptly loaded onto a gel filtration column (AcA44) to remove unconjugated ribosome-inactivating protein. Purification was completed using soft gel affinity chromatography on Blue Toyopearl® resin using a method similar to Knowles et al., *Analyt. Biochem.*, 160, 440 (1987). Samples of the final product were run on 5% non-reduced SDS PAGE, Coomassie stained, and scanned with a Shimadzu laser densitometer to quantitate the number of toxins per antibody. The conjugation efficiency was substantially greater for $BRIP_{C277}$ (78%) than for either of the other two analogs, $BRIP_{C270}$ and $BRIP_{C256}$ (each of these was about 10%). Additionally, the $BRIP_{C277}$ product was a polyconjugate, i.e., several BRIP molecules conjugated to a single antibody, in contrast to the $BRIP_{C270}$ and $BRIP_{C256}$ products which were monoconjugates.

Whole Cell Kill Assay

Immunoconjugates of native BRIP and of the BRIP analogs were tested for the ability to inhibit protein synthesis in HSB2 cells by the whole cell kill assay described in Example 1. Standard immunoconjugates H65-RTA (H65 derivatized with SPDP linked to RTA) and 4MRTA (4A2 antibody derivatized with M2IT linked to RTA) and BRIP immunoconjugate samples were diluted with RPMI without leucine at half-log concentrations ranging from 2000 to 0.632 ng/ml. All dilutions were added in triplicate to microtiter plates containing $1\times10^5$ HSB2 cells. HSB2 plates were incubated for 20 hours at 37° C. and then pulsed with $^3$H-Leu for 4 hours before harvesting. Samples were counted on the Inotec Trace 96 cascade ionization counter. By comparison with an untreated sample, the picomolar toxin concentration (pM T) of immunoconjugate which resulted in a 50% inhibition of protein synthesis (IC$_{50}$) was calculated. The assay results are presented below in Table 8.

TABLE 8

| Conjugate | IC$_{50}$ (pM T) |
|---|---|
| 4A2-BRIP | 122.45 |
| 4A2-BRIP$_{C270}$ | 46.3 |
| 4A2-BRIP$_{C277}$ | 57.5 |
| 4A2-BRIP$_{C256}$ | 1116 |
| H65-BRIP | >5000 |
| H65-BRIP$_{C277}$ | 1176 |

The BRIP analog conjugates were less potent than the ricin conjugate control (data not shown). The immunotoxins containing antibody 4A2 and either the BRIP$_{C270}$ or the BRIP$_{C277}$ analog exhibited comparable to increased specific cytotoxicity toward target cells as compared to immunotoxin containing native BRIP. While 4A2-BRIP$_{C256}$ is less active than 4A2-BRIP, 4A2-BRIP$_{C270}$ and 4A2-BRIP$_{C277}$ are between 3 and 4 times more active. Similarly, the immunoconjugate of H65 to BRIP$_{C277}$ shows greater toxicity toward target cells than the immunoconjugate of H65 to native BRIP. Thus, linkage of antibody to BRIP derivatives which have an available cysteine residue in an appropriate location results in immunotoxins with enhanced specific toxicity toward target cells relative to conjugates with native BRIP.

Disulfide Bond Stability Assay

Immunoconjugates prepared with native BRIP and the BRIP analogs were examined by the disulfide bond stability assay described in Example 1. Briefly, conjugates were incubated with increasing concentrations of glutathione for 1 hour at 37° C. and, after terminating the reaction with iodoacetamide, the amount of RIP released was quantitated by size-exclusion HPLC on a TosoHaas TSK-G2000SW column.

By comparisons with the amount of RIP released by high concentrations of 2-mercaptoethanol (to determine 100% release), the concentration of glutathione required to release 50% of the RIP (the RC$_{50}$) was calculated. As shown below in Table 9, the conjugates prepared with BRIP$_{C270}$ or BRIP$_{C277}$ were significantly more stable than either the RTA conjugates or those prepared with native BRIP.

TABLE 9

| Conjugate | RC$_{50}$ (mM) |
|---|---|
| H65-RTA | 7.0 |
| H65-BRIP | 2.8 |
| H65-BRIP$_{C277}$ | 196.0 |
| 4A2-RTA | 4.4 |
| 4A2-BRIP | 3.3 |
| 4A2-BRIP$_{C270}$ | 53.0 |
| 4A2-BRIP$_{C277}$ | 187.0 |

These unexpected results suggest that conjugates prepared with Type I RIP analogs according to the present invention may have enhanced stability and efficacy in vivo.

Example 3

Plants of the genus *Momordica* produce a number of related proteins known as momordins or momorcharins which are Type I RIPs. The gene encoding momordin II was cloned from *Momordica balsamina* seeds.

Preparation of M. balsamina RNA

Total RNA was prepared from 4 g of *M. balsamina* seeds as described in Ausubel et al., supra. PolyA containing RNA was prepared from 1 mg of total RNA by chromatography on oligo-(dT)-cellulose. 40 mg of oligo-(dT)-cellulose Type 7 (Pharmacia) was added to 0.1 N NaOH and poured into a disposable column (Biorad). The column was washed with water until the eluate was pH 5.5, and then was washed with 1X loading buffer (50 mM NaCitrate, 0.5M NaCl, 1 mM EDTA, 0.1% SDS, pH 7.0) until the eluate was pH 7.0. 1 mg of total RNA was suspended in 300 µl of water, heated to 65° C. for 5 minutes, and 300 µl of 2X loading buffer was added (100 mM Na Citrate, 1M NaCl, 2 mM EDTA, and 0.2% SDS). The RNA was loaded onto the column, and the flow through was reheated to 65° C., cooled to room temperature, and reloaded onto the column. Column-bound mRNA was washed 5 times with 0.5 ml of 1X loading buffer, and two times with 0.5 ml of 0.05M NaCitrate, 0.1 M NaCl, 1 mM EDTA, 0.1% SDS. PolyA-containing RNA was eluted two times from the column with 0.5 ml of 25 mM NaCitrate, 1 mM EDTA, and 0.05% SDS.

Library Preparation

A cDNA library from the polyA-containing *M. balsamina* RNA was prepared in a bacterial expression plasmid with the SuperScript Plasmid System (BRL, Gaithersburg, Md.). The cDNA was synthesized from 2 µg of poly A-containing RNA, size fractionated, digested with NotI, and ligated into the expression vector pSPORT as recommended by the manufacturer of the vector, BRL.

Cloning of the Momordin II Gene

A DNA fragment encoding the first 27 amino acids of momordin II was amplified from *M. balsamina* cDNA by PCR. First strand cDNA was prepared from 100 ng of polyA containing RNA with an RNA-PCR Kit (Perkin Elmer Cetus). Two partially degenerate primers were synthesized based on the amino acid sequence of the first 27 amino acids of momordin II described in Li et al., *Experientia*, 36, 524–527 (1980). Because the amino acid sequence of amino acids 1–27 of momordin II is 52% homologous to amino acids 1–17 of momordin I [Ho et al., BBA, 1088, 311–314 (1991)], some codon assignments in the degenerate primers were based on homology to the corresponding amino acid as well as codon preference in the momordin I gene. The sequences of primers momo-3 and momo-4 are set out below using IUPAC nucleotide symbols.

momo-3 (SEQ ID NO: 52)
5' GATGTTAAYTTYGAYTTGTCNACDGCTAC 3' momo-4 (SEQ ID NO: 53)
5' ATTGGNAGDGTAGCCCTRAARTCYTCDAT 3'

The resulting 81 bp PCR product was purified on a 5% acrylamide gel and cloned into the SmaI site of pUC18. Three candidate clones were sequenced, and one clone, pMO110, was identified which encoded the N-terminal 27 amino acids of momordin II.

A hybridization probe was designed for screening of the momordin II cDNA library based on the sequence of the pMO110 momordinII DNA fragment. The sequence of the primer momo-5 is shown below.

momo-5 (SEQ ID NO: 54)
5' GCCAC<u>TGCAAAAACCTACACAAAATTT</u>ATTGA 3'

Primer momo-5 corresponds to amino acids 9–18 of mature momordin II. The underlined nucleotides of the primer were expected to match the DNA sequence of the momordin II gene exactly. Since this sequence is highly A/T-rich and may hybridize to the momordin II gene weakly, the additional adjacent nucleotides were included in the primer. Bases 3 and 30 (overlined) were in the "wobble" position (i.e., the third nucleotide in a codon) of amino acids 9 (alanine) and 18 (isoleucine), respectively, of momordin II and may not be identical to the nucleotide bases in the native gene.

A 90,000 member cDNA library in pSPORT was screened with $^{32}$P-kinased momo-5, and eight potential candidate clones were identified. One clone, pING3619, was sequenced and contains an open reading frame corresponding in part to the expected N-terminal 27 residues of Momordin II. The complete momordin gene contains 286 amino acids, the first 23 of which are a presumed leader signal (mature momordin II is 263 residues). The DNA sequence of the momordin II gene is set out in SEQ ID NO: 13 and in FIG. 12.

Construction of an Expression Vector Containing the Momordin II Gene

A bacterial expression vector for the momordin II gene was constructed. Two PCR primers were synthesized, one (momo-9) which primes from the +1 residue of the mature momordin II amino acid sequence, and one at the C-terminus (momo-10) of momordin II which introduces an XhoI restriction site:

momo-9 (SEQ ID NO: 55)
5' GATGTTAACTTCGATTTGTCGA 3' momo-10 (SEQ ID NO: 56)
5' TCAACTCGAGGTACTCAATTCACAACAGATTCC 3' pING3619 was amplified with momo-9 and momo-10, and the product was treated with T4 polymerase, cut with XhoI, and purified on an agarose gel. This gene fragment was ligated along with the 131 bp pelB leader fragment from pIC100 which has been generated by SstI digestion, T4-polymerase treatment, and EcoRI digestion, into the araB expression vector cleaved with EcoRI and XhoI. The product of this three piece ligation was sequenced to verify that the pelB junction and momordin II coding sequence were correct. Arabinose induction of cells containing the momordin II expression plasmid pING3621 results in production of momordin II in *E. coli*.

Analogs of Mormordin II

Mormordin II has no natural cysteines available for conjugation to antibody. Analogs of momordin which have a free cysteine for conjugation to an antibody may be constructed. Positions likely to be appropriate for substitution of a cysteine residue may be identified from FIG. 3 as positions near the ricin A-chain cysteine$_{259}$ and as positions including the last 26 amino acids of momordin II that are accessible to solvent. For example, the arginine at position 242 of momordin II aligns with the ricin A-chain cysteine at position 259 and is a preferred target for substitution. Additional preferred substitution positions for momordin II include the serine at position 241 and the alanine at position 243.

While the present invention has been described in terms of preferred embodiments, it is understood that variations and improvements will occur to those skilled in the art. Therefore, it is intended that the appended claims cover all such equivalent variations which come within the scope of the invention as claimed.

---

We claim:

1. A non-naturally occurring analog of the Type I ribosome-inactivating protein, gelonin, wherein a cysteine is substituted for another amino acid at an amino acid position not naturally available for intermolecular disulfide bonding in said gelonin and said cysteine being available for intermolecular disulfide bonding, wherein said cysteine is substituted at an amino acid position in said gelonin from position 239 to the carboxy terminus, wherein said analog retains ribosome-inactivating activity of said gelonin, and wherein said gelonin comprises the amino acid sequence shown in SEQ ID NO: 2.

2. The gelonin analog recited in claim 1 wherein said cysteine is substituted at a position selected from the group consisting of positions 239, 244, 247, and 248 of the amino sequence of said analog.

3. The gelonin analog recited in claim 1 or 2 wherein additionally the native gelonin cysteine residues at positions 44 and 50 are replaced with alanine residues.

4. A non-naturally occurring analog of barley ribosome-inactivating protein wherein a cysteine is substituted for another amino acid at an amino acid position not naturally available for intermolecular disulfide bonding in said barley ribosome-inactivating protein and said cysteine being available for intermolecular disulfide bonding and wherein said cysteine is substituted at an amino acid position in said barley ribsome-inactivating protein from position 256 to the carboxy terminus, wherein said analog retains ribosome-inactivating of said barley ribosome-inactivating protein, and wherein said barley ribosome-inactivating protein comprises the amino acid sequence shown in SEQ ID NO: 3.

5. The barley ribosome-inactivating protein analog recited in claim 4 wherein said cysteine is at position 256 of the amino acid sequence of said analog.

6. The barley ribosome-inactivating protein analog recited in claim 4 wherein said cysteine is substituted at position 270 of the amino acid sequence of said analog.

7. The barley ribosome-inactivating protein analog recited in claim 4 wherein said cysteine is substituted at position 277 of the amino acid of said analog.

8. An analog of the Type I ribosome-inactivating protein, gelonin, comprising a cysteine residue substituted for a non-cysteine residue at position 10 in the amino acid sequence shown in SEQ ID NO: 2.

9. An analog of the Type I ribosome-inactivating protein, gelonin, comprising a cysteine residue substituted for a non-cysteine residue at position 60 in the amino acid sequence shown in SEQ ID NO: 2.

10. An analog of the Type I ribosome-inactivating protein, gelonin, comprising a cysteine residue substituted for a non-cysteine residue at position 50 in the amino acid sequence shown in SEQ ID NO: 2.

11. An analog of the Type I ribosome-inactivating protein, gelonin, comprising a cysteine residue substituted for a non-cysteine residue at position 44 in the amino acid sequence shown in SEQ ID NO: 2.

* * * * *

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 267 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ile  Phe  Pro  Lys  Gln  Tyr  Pro  Ile  Ile  Asn  Phe  Thr  Thr  Ala  Gly  Ala
 1              5                        10                        15

Thr  Val  Gln  Ser  Tyr  Thr  Asn  Phe  Ile  Arg  Ala  Val  Arg  Gly  Arg  Leu
               20                        25                        30

Thr  Thr  Gly  Ala  Asp  Val  Arg  His  Glu  Ile  Pro  Val  Leu  Pro  Asn  Arg
          35                        40                        45

Val  Gly  Leu  Pro  Ile  Asn  Gln  Arg  Phe  Ile  Leu  Val  Glu  Leu  Ser  Asn
     50                        55                        60

His  Ala  Glu  Leu  Ser  Val  Thr  Leu  Ala  Leu  Asp  Val  Thr  Asn  Ala  Tyr
 65                        70                        75                        80

Val  Val  Gly  Tyr  Arg  Ala  Gly  Asn  Ser  Ala  Tyr  Phe  Phe  His  Pro  Asp
               85                        90                        95

Asn  Gln  Glu  Asp  Ala  Glu  Ala  Ile  Thr  His  Leu  Phe  Thr  Asp  Val  Gln
              100                       105                       110

Asn  Arg  Tyr  Thr  Phe  Ala  Phe  Gly  Gly  Asn  Tyr  Asp  Arg  Leu  Glu  Gln
```

|     |     | 115 |     |     |     | 120 |     |     |     | 125 |     |     |
| --- | --- | --- | --- | --- | --- | --- | --- | --- | --- | --- | --- | --- |
| Leu | Ala | Gly | Asn | Leu | Arg | Glu | Asn | Ile | Glu | Leu | Gly | Asn | Gly | Pro | Leu |
|     |     | 130 |     |     |     | 135 |     |     |     | 140 |     |     |
| Glu | Glu | Ala | Ile | Ser | Ala | Leu | Tyr | Tyr | Tyr | Ser | Thr | Gly | Gly | Thr | Gln |
| 145 |     |     |     |     | 150 |     |     |     |     | 155 |     |     |     |     | 160 |
| Leu | Pro | Thr | Leu | Ala | Arg | Ser | Phe | Ile | Ile | Cys | Ile | Gln | Met | Ile | Ser |
|     |     |     |     | 165 |     |     |     |     | 170 |     |     |     |     | 175 |     |
| Glu | Ala | Ala | Arg | Phe | Gln | Tyr | Ile | Glu | Gly | Glu | Met | Arg | Thr | Arg | Ile |
|     |     |     | 180 |     |     |     |     | 185 |     |     |     |     | 190 |     |     |
| Arg | Tyr | Asn | Arg | Arg | Ser | Ala | Pro | Asp | Pro | Ser | Val | Ile | Thr | Leu | Glu |
|     |     | 195 |     |     |     |     | 200 |     |     |     |     | 205 |     |     |     |
| Asn | Ser | Trp | Gly | Arg | Leu | Ser | Thr | Ala | Ile | Gln | Glu | Ser | Asn | Gln | Gly |
|     |     | 210 |     |     |     |     | 215 |     |     |     |     | 220 |     |     |     |
| Ala | Phe | Ala | Ser | Pro | Ile | Gln | Leu | Gln | Arg | Arg | Asn | Gly | Ser | Lys | Phe |
| 225 |     |     |     |     | 230 |     |     |     |     | 235 |     |     |     |     | 240 |
| Ser | Val | Tyr | Asp | Val | Ser | Ile | Leu | Ile | Pro | Ile | Ile | Ala | Leu | Met | Val |
|     |     |     |     | 245 |     |     |     |     | 250 |     |     |     |     | 255 |     |
| Tyr | Arg | Cys | Ala | Pro | Pro | Pro | Ser | Ser | Gln | Phe |
|     |     |     | 260 |     |     |     |     | 265 |     |     |

( 2 ) INFORMATION FOR SEQ ID NO:2:

( i ) SEQUENCE CHARACTERISTICS:
( A ) LENGTH: 251 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Gly | Leu | Asp | Thr | Val | Ser | Phe | Ser | Thr | Lys | Gly | Ala | Thr | Tyr | Ile | Thr |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Tyr | Val | Asn | Phe | Leu | Asn | Glu | Leu | Arg | Val | Lys | Leu | Lys | Pro | Glu | Gly |
|     |     |     | 20 |     |     |     |     | 25 |     |     |     |     | 30 |     |     |
| Asn | Ser | His | Gly | Ile | Pro | Leu | Leu | Arg | Lys | Lys | Cys | Asp | Asp | Pro | Gly |
|     |     | 35 |     |     |     |     | 40 |     |     |     |     | 45 |     |     |     |
| Lys | Cys | Phe | Val | Leu | Val | Ala | Leu | Ser | Asn | Asp | Asn | Gly | Gln | Leu | Ala |
| 50 |     |     |     |     | 55 |     |     |     |     | 60 |     |     |     |     |     |
| Glu | Ile | Ala | Ile | Asp | Val | Thr | Ser | Val | Tyr | Val | Val | Gly | Tyr | Gln | Val |
| 65 |     |     |     |     | 70 |     |     |     |     | 75 |     |     |     |     | 80 |
| Arg | Asn | Arg | Ser | Tyr | Phe | Phe | Lys | Asp | Ala | Pro | Asp | Ala | Ala | Tyr | Glu |
|     |     |     |     | 85 |     |     |     |     | 90 |     |     |     |     | 95 |     |
| Gly | Leu | Phe | Lys | Asn | Thr | Ile | Lys | Thr | Arg | Leu | His | Phe | Gly | Gly | Thr |
|     |     |     | 100 |     |     |     |     | 105 |     |     |     |     | 110 |     |     |
| Tyr | Pro | Ser | Leu | Glu | Gly | Glu | Lys | Ala | Tyr | Arg | Glu | Thr | Thr | Asp | Leu |
|     |     |     | 115 |     |     |     |     | 120 |     |     |     |     | 125 |     |     |
| Gly | Ile | Glu | Pro | Leu | Arg | Ile | Gly | Ile | Lys | Lys | Leu | Asp | Glu | Asn | Ala |
|     |     | 130 |     |     |     |     | 135 |     |     |     |     | 140 |     |     |     |
| Ile | Asp | Asn | Tyr | Lys | Pro | Thr | Glu | Ile | Ala | Ser | Ser | Leu | Leu | Val | Val |
| 145 |     |     |     |     | 150 |     |     |     |     | 155 |     |     |     |     | 160 |
| Ile | Gln | Met | Val | Ser | Glu | Ala | Ala | Arg | Phe | Thr | Phe | Ile | Glu | Asn | Gln |
|     |     |     |     | 165 |     |     |     |     | 170 |     |     |     |     | 175 |     |
| Ile | Arg | Asn | Asn | Phe | Gln | Gln | Arg | Ile | Arg | Pro | Ala | Asn | Asn | Thr | Ile |
|     |     |     | 180 |     |     |     |     | 185 |     |     |     |     | 190 |     |     |
| Ser | Leu | Glu | Asn | Lys | Trp | Gly | Lys | Leu | Ser | Phe | Gln | Ile | Arg | Thr | Ser |
|     |     | 195 |     |     |     |     | 200 |     |     |     |     | 205 |     |     |     |
| Gly | Ala | Asn | Gly | Met | Phe | Ser | Glu | Ala | Val | Glu | Leu | Glu | Arg | Ala | Asn |
|     |     | 210 |     |     |     |     | 215 |     |     |     |     | 220 |     |     |     |

```
    Gly  Lys  Lys  Tyr  Tyr  Val  Thr  Ala  Val  Asp  Gln  Val  Lys  Pro  Lys  Ile
    225                230                     235                          240

Ala  Leu  Leu  Lys  Phe  Val  Asp  Lys  Asp  Pro  Lys
                       245                250
```

( 2 ) INFORMATION FOR SEQ ID NO:3:

( i ) SEQUENCE CHARACTERISTICS:
        ( A ) LENGTH: 280 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
    Ala  Ala  Lys  Met  Ala  Lys  Asn  Val  Asp  Lys  Pro  Leu  Phe  Thr  Ala  Thr
    1              5                    10                       15

Phe  Asn  Val  Gln  Ala  Ser  Ser  Ala  Asp  Tyr  Ala  Thr  Phe  Ile  Ala  Gly
                   20                  25                       30

Ile  Arg  Asn  Lys  Leu  Arg  Asn  Pro  Ala  His  Phe  Ser  His  Asn  Arg  Pro
              35                       40                       45

Val  Leu  Pro  Pro  Val  Glu  Pro  Asn  Val  Pro  Pro  Ser  Arg  Trp  Phe  His
         50                       55                       60

Val  Val  Leu  Lys  Ala  Ser  Pro  Thr  Ser  Ala  Gly  Leu  Thr  Leu  Ala  Ile
    65                       70                       75                       80

Arg  Ala  Asp  Asn  Ile  Tyr  Leu  Glu  Gly  Phe  Lys  Ser  Ser  Asp  Gly  Thr
                        85                       90                       95

Trp  Trp  Glu  Leu  Thr  Pro  Gly  Leu  Ile  Pro  Gly  Ala  Thr  Tyr  Val  Gly
                   100                      105                      110

Phe  Gly  Gly  Thr  Tyr  Arg  Asp  Leu  Leu  Gly  Asp  Thr  Asp  Lys  Leu  Thr
              115                      120                      125

Asn  Val  Ala  Leu  Gly  Arg  Gln  Gln  Leu  Ala  Asp  Ala  Val  Thr  Ala  Leu
         130                      135                      140

His  Gly  Arg  Thr  Lys  Ala  Asp  Lys  Ala  Ser  Gly  Pro  Lys  Gln  Gln  Gln
    145                      150                      155                      160

Ala  Arg  Glu  Ala  Val  Thr  Thr  Leu  Val  Leu  Met  Val  Asn  Glu  Ala  Thr
                        165                      170                      175

Arg  Phe  Gln  Thr  Val  Ser  Gly  Phe  Val  Ala  Gly  Leu  Leu  His  Pro  Lys
                   180                      185                      190

Ala  Val  Glu  Lys  Lys  Ser  Gly  Lys  Ile  Gly  Asn  Glu  Met  Lys  Ala  Gln
              195                      200                      205

Val  Asn  Gly  Trp  Gln  Asp  Leu  Ser  Ala  Ala  Leu  Leu  Lys  Thr  Asp  Val
         210                      215                      220

Lys  Pro  Pro  Pro  Gly  Lys  Ser  Pro  Ala  Lys  Phe  Ala  Pro  Ile  Glu  Lys
    225                      230                      235                      240

Met  Gly  Val  Arg  Thr  Ala  Glu  Gln  Ala  Ala  Asn  Thr  Leu  Gly  Ile  Leu
                        245                      250                      255

Leu  Phe  Val  Glu  Val  Pro  Gly  Gly  Leu  Thr  Val  Ala  Lys  Ala  Leu  Glu
                   260                      265                      270

Leu  Phe  His  Ala  Ser  Gly  Gly  Lys
                   275                 280
```

( 2 ) INFORMATION FOR SEQ ID NO:4:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Asp | Val | Asn | Phe | Asp | Leu | Ser | Thr | Ala | Thr | Ala | Lys | Thr | Tyr | Thr | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Ile | Glu | Asp | Phe | Arg | Ala | Thr | Leu | Pro | Phe | Ser | His | Lys | Val | Tyr |
|     |     |     | 20  |     |     |     |     | 25  |     |     |     |     | 30  |     |     |

| Asp | Ile | Pro | Leu | Leu | Tyr | Ser | Thr | Ile | Ser | Asp | Ser | Arg | Arg | Phe | Ile |
|     |     | 35  |     |     |     |     | 40  |     |     |     |     | 45  |     |     |     |

| Leu | Leu | Asp | Leu | Thr | Ser | Tyr | Ala | Tyr | Glu | Thr | Ile | Ser | Val | Ala | Ile |
|     | 50  |     |     |     |     | 55  |     |     |     |     | 60  |     |     |     |     |

| Asp | Val | Thr | Asn | Val | Tyr | Val | Val | Ala | Tyr | Arg | Thr | Arg | Asp | Val | Ser |
| 65  |     |     |     |     | 70  |     |     |     |     | 75  |     |     |     |     | 80  |

| Tyr | Phe | Phe | Lys | Glu | Ser | Pro | Pro | Glu | Ala | Tyr | Asn | Ile | Leu | Phe | Lys |
|     |     |     |     | 85  |     |     |     |     | 90  |     |     |     |     | 95  |     |

| Gly | Thr | Arg | Lys | Ile | Thr | Leu | Pro | Tyr | Thr | Gly | Asn | Tyr | Glu | Asn | Leu |
|     |     |     | 100 |     |     |     |     | 105 |     |     |     |     | 110 |     |     |

| Gln | Thr | Ala | Ala | His | Lys | Ile | Arg | Glu | Asn | Ile | Asp | Leu | Gly | Leu | Pro |
|     |     |     | 115 |     |     |     |     | 120 |     |     |     |     | 125 |     |     |

| Ala | Leu | Ser | Ser | Ala | Ile | Thr | Thr | Leu | Phe | Tyr | Tyr | Asn | Ala | Gln | Ser |
|     | 130 |     |     |     |     |     | 135 |     |     |     |     | 140 |     |     |     |

| Ala | Pro | Ser | Ala | Leu | Leu | Val | Leu | Ile | Gln | Thr | Thr | Ala | Glu | Ala | Ala |
| 145 |     |     |     |     | 150 |     |     |     |     | 155 |     |     |     |     | 160 |

| Arg | Phe | Lys | Tyr | Ile | Glu | Arg | His | Val | Ala | Lys | Tyr | Val | Ala | Thr | Asn |
|     |     |     |     | 165 |     |     |     |     | 170 |     |     |     |     | 175 |     |

| Phe | Lys | Pro | Asn | Leu | Ala | Ile | Ile | Ser | Leu | Glu | Asn | Gln | Trp | Ser | Ala |
|     |     |     | 180 |     |     |     |     | 185 |     |     |     |     | 190 |     |     |

| Leu | Ser | Lys | Gln | Ile | Phe | Leu | Ala | Gln | Asn | Gln | Gly | Gly | Lys | Phe | Arg |
|     |     | 195 |     |     |     |     | 200 |     |     |     |     | 205 |     |     |     |

| Asn | Pro | Val | Asp | Leu | Ile | Lys | Pro | Thr | Gly | Glu | Arg | Phe | Gln | Val | Thr |
|     | 210 |     |     |     |     | 215 |     |     |     |     | 220 |     |     |     |     |

| Asn | Val | Asp | Ser | Asp | Val | Val | Lys | Gly | Asn | Ile | Lys | Leu | Leu | Leu | Asn |
| 225 |     |     |     |     | 230 |     |     |     |     | 235 |     |     |     |     | 240 |

| Ser | Arg | Ala | Ser | Thr | Ala | Asp | Glu | Asn | Phe | Ile | Thr | Thr | Met | Thr | Leu |
|     |     |     |     | 245 |     |     |     |     | 250 |     |     |     |     | 255 |     |

| Leu | Gly | Glu | Ser | Val | Val | Asn |
|     |     |     | 260 |     |     |     |

( 2 ) INFORMATION FOR SEQ ID NO:5:

( i ) SEQUENCE CHARACTERISTICS:
        ( A ) LENGTH: 248 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Asp | Val | Arg | Phe | Ser | Leu | Ser | Gly | Ser | Ser | Thr | Ser | Tyr | Ser | Lys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Ile | Gly | Asp | Leu | Arg | Lys | Ala | Leu | Pro | Ser | Asn | Gly | Thr | Val | Tyr |
|     |     |     | 20  |     |     |     |     | 25  |     |     |     |     | 30  |     |     |

| Asn | Leu | Thr | Ile | Leu | Leu | Ser | Ser | Ala | Ser | Gly | Ala | Ser | Arg | Tyr | Thr |
|     |     | 35  |     |     |     |     | 40  |     |     |     |     | 45  |     |     |     |

| Leu | Met | Thr | Leu | Ser | Asn | Tyr | Asp | Gly | Lys | Ala | Ile | Thr | Val | Ala | Val |
|     | 50  |     |     |     |     | 55  |     |     |     |     | 60  |     |     |     |     |

| Asp | Val | Ser | Gln | Leu | Tyr | Ile | Met | Gly | Tyr | Leu | Val | Asn | Ser | Thr | Ser |
| 65  |     |     |     |     | 70  |     |     |     |     | 75  |     |     |     |     | 80  |

| Tyr | Phe | Phe | Asn | Glu | Ser | Asp | Ala | Lys | Leu | Ala | Ser | Gln | Tyr | Val | Phe |

|        |        |        |        |        | 85     |        |        |        |        | 90     |        |        |        |        | 95     |
|--------|--------|--------|--------|--------|--------|--------|--------|--------|--------|--------|--------|--------|--------|--------|--------|

Lys Gly Ser Thr Ile Val Thr Leu Pro Tyr Ser Gly Asn Tyr Glu Lys
             100                 105                 110

Leu Gln Thr Ala Ala Gly Lys Ile Arg Glu Lys Ile Pro Leu Gly Phe
             115                 120                 125

Pro Ala Leu Asp Ser Ala Leu Thr Thr Ile Phe His Tyr Asp Ser Thr
             130                 135                 140

Ala Ala Ala Ala Ala Phe Leu Val Ile Leu Gln Thr Thr Ala Glu Ala
145                  150                 155                 160

Ser Arg Phe Lys Tyr Ile Glu Gly Gln Ile Ile Glu Arg Ile Ser Lys
             165                 170                 175

Asn Gln Val Pro Ser Leu Ala Thr Ile Ser Leu Glu Asn Ser Leu Trp
             180                 185                 190

Ser Ala Leu Ser Lys Gln Ile Gln Leu Ala Gln Thr Asn Asn Gly Thr
             195                 200                 205

Phe Lys Thr Pro Val Val Ile Thr Asp Asp Lys Gly Gln Arg Val Glu
    210                 215                 220

Ile Thr Asn Val Thr Ser Lys Val Val Thr Lys Asn Ile Gln Leu Leu
225                 230                 235                 240

Leu Asn Tyr Lys Gln Asn Val Ala
             245

( 2 ) INFORMATION FOR SEQ ID NO:6:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Lys Leu Tyr
             20                  25                  30

Asp Leu Pro Leu Ile Arg Ser Ser Leu Pro Gly Ser Gln Arg Tyr Ala
             35                  40                  45

Ile Ile His Leu Thr Asn Tyr Ala Asp Glu Val Ala Leu Asp Val Thr
        50                  55                  60

Asn Val Asp Ala Gly Leu Pro Arg Asn Ala Val Leu Tyr Ile Met Gly
65                  70                  75                  80

Tyr Arg Ala Gly Asp Thr Ser Tyr Phe Phe Asn Glu Ala Ser Ala Thr
                85                  90                  95

Glu Ala Ala Lys Tyr Val Phe Lys Asp Ala Met Arg Lys Val Thr Leu
             100                 105                 110

Pro Tyr Ser Gly Asn Tyr Glu Arg Leu Gln Thr Ala Ala Gly Gly Leu
             115                 120                 125

Arg Glu Asn Ile Pro Leu Gly Leu Pro Ala Leu Asp Ser Ala Ile Thr
    130                 135                 140

Thr Leu Phe Tyr Tyr Asn Ala Asn Ser Ala Ala Ser Ala Leu Met Val
145                 150                 155                 160

Leu Ile Gln Ser Thr Ser Glu Ala Ala Arg Tyr Lys Phe Ile Glu Gln
             165                 170                 175

Gln Ile Gly Ser Arg Val Asp Lys Thr Phe Leu Pro Ser Leu Ala Ile
             180                 185                 190

Ile Ser Leu Glu Asn Ser Leu Trp Leu Ala Leu Ser Lys Gln Ile Gln
             195                 200                 205

```
Ile Ala Ser Thr Asn Asn Gly Glu Phe Glu Thr Pro Val Val Leu Ile
    210                 215                 220

Asn Ala Gln Asn Gln Arg Val Thr Ile Thr Asn Val Asp Ala Gly Val
225                 230                 235                 240

Val Thr Ser Asn Ile Ala Leu Leu Leu Asn Arg Asn Asn Met Ala
                245                 250                 255
```

(2) INFORMATION FOR SEQ ID NO:7:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:7:

```
Asp Val Ser Phe Arg Leu Ser Gly Ala Asp Pro Arg Ser Tyr Gly Met
1               5                   10                  15

Phe Ile Lys Asp Leu Arg Asn Ala Leu Pro Phe Arg Glu Lys Val Tyr
                20                  25                  30

Asn Ile Pro Leu Leu Leu Pro Ser Val Ser Gly Ala Gly Arg Tyr Leu
            35                  40                  45

Leu Met His Leu Phe Asn Tyr Asp Gly Lys Thr Ile Thr Val Ala Val
        50                  55                  60

Asp Val Thr Asn Val Tyr Ile Met Gly Tyr Leu Ala Asp Thr Thr Ser
65                  70                  75                  80

Tyr Phe Phe Asn Glu Pro Ala Ala Glu Leu Ala Ser Gln Tyr Val Phe
                85                  90                  95

Arg Asp Ala Arg Arg Lys Ile Thr Leu Pro Tyr Ser Gly Asn Tyr Glu
                100                 105                 110

Arg Leu Gln Ile Ala Ala Gly Lys Pro Arg Glu Lys Ile Pro Ile Gly
            115                 120                 125

Leu Pro Ala Leu Asp Ser Ala Ile Ser Thr Leu Leu His Tyr Asp Ser
    130                 135                 140

Thr Ala Ala Ala Gly Ala Leu Leu Val Leu Ile Gln Thr Thr Ala Glu
145                 150                 155                 160

Ala Ala Arg Phe Lys Tyr Ile Glu Gln Gln Ile Gln Glu Arg Ala Tyr
                165                 170                 175

Arg Asp Glu Val Pro Ser Leu Ala Thr Ile Ser Leu Glu Asn Ser Trp
                180                 185                 190

Ser Gly Leu Ser Lys Gln Ile Gln Leu Ala Gln Gly Asn Asn Gly Ile
            195                 200                 205

Phe Arg Thr Pro Ile Val Leu Val Asp Asn Lys Gly Asn Arg Val Gln
    210                 215                 220

Ile Thr Asn Val Thr Ser Lys Val Val Thr Ser Asn Ile Gln Leu Leu
225                 230                 235                 240

Leu Asn Thr Arg Asn Ile Ala Glu Gly Asp Asn Gly Asp Val Ser Thr
                245                 250                 255

Thr His Gly Phe Ser Ser Thr
            260
```

(2) INFORMATION FOR SEQ ID NO:8:

(i) SEQUENCE CHARACTERISTICS:
        (A) LENGTH: 250 amino acids
        (B) TYPE: amino acid
        (D) TOPOLOGY: linear (ii) MOLECULE TYPE: protein ( x i ) SEQUENCE DESCRIPTION: SEQ ID NO:8:

| Ala | Pro | Thr | Leu | Glu | Thr | Ile | Ala | Ser | Leu | Asp | Leu | Asn | Asn | Pro | Thr |
| 1 | | | | 5 | | | | | 10 | | | | | 15 | |

| Thr | Tyr | Leu | Ser | Phe | Ile | Thr | Asn | Ile | Arg | Thr | Lys | Val | Ala | Asp | Lys |
| | | | 20 | | | | | 25 | | | | | 30 | | |

| Thr | Glu | Gln | Cys | Thr | Ile | Gln | Lys | Ile | Ser | Lys | Thr | Phe | Thr | Gln | Arg |
| | | 35 | | | | | 40 | | | | | 45 | | | |

| Tyr | Ser | Tyr | Ile | Asp | Leu | Ile | Val | Ser | Ser | Thr | Gln | Lys | Ile | Thr | Leu |
| | 50 | | | | | 55 | | | | | 60 | | | | |

| Ala | Ile | Asp | Met | Ala | Asp | Leu | Tyr | Val | Leu | Gly | Tyr | Ser | Asp | Ile | Ala |
| 65 | | | | | 70 | | | | | 75 | | | | | 80 |

| Asn | Asn | Lys | Gly | Arg | Ala | Phe | Phe | Phe | Lys | Asp | Val | Thr | Glu | Ala | Val |
| | | | | 85 | | | | | 90 | | | | | 95 | |

| Ala | Asn | Asn | Phe | Phe | Pro | Gly | Ala | Thr | Gly | Thr | Asn | Arg | Ile | Lys | Leu |
| | | | 100 | | | | | 105 | | | | | 110 | | |

| Thr | Phe | Thr | Gly | Ser | Tyr | Gly | Asp | Leu | Glu | Lys | Asn | Gly | Gly | Leu | Arg |
| | | 115 | | | | | 120 | | | | | 125 | | | |

| Lys | Asp | Asn | Pro | Leu | Gly | Ile | Phe | Arg | Leu | Glu | Asn | Ser | Ile | Val | Asn |
| | 130 | | | | | 135 | | | | | 140 | | | | |

| Ile | Tyr | Gly | Lys | Ala | Gly | Asp | Val | Lys | Lys | Gln | Ala | Lys | Phe | Phe | Leu |
| 145 | | | | | 150 | | | | | 155 | | | | | 160 |

| Leu | Ala | Ile | Gln | Met | Val | Ser | Glu | Ala | Ala | Arg | Phe | Lys | Tyr | Ile | Ser |
| | | | | 165 | | | | | 170 | | | | | 175 | |

| Asp | Lys | Ile | Pro | Ser | Glu | Lys | Tyr | Glu | Glu | Val | Thr | Val | Asp | Glu | Tyr |
| | | | 180 | | | | | 185 | | | | | 190 | | |

| Met | Thr | Ala | Leu | Glu | Asn | Asn | Trp | Ala | Lys | Leu | Ser | Thr | Ala | Val | Tyr |
| | | 195 | | | | | 200 | | | | | 205 | | | |

| Asn | Ser | Lys | Pro | Ser | Thr | Thr | Thr | Ala | Thr | Lys | Cys | Gln | Leu | Ala | Thr |
| | 210 | | | | | 215 | | | | | 220 | | | | |

| Ser | Pro | Val | Thr | Ile | Ser | Pro | Trp | Ile | Phe | Lys | Thr | Val | Glu | Glu | Ile |
| 225 | | | | | 230 | | | | | 235 | | | | | 240 |

| Lys | Leu | Val | Met | Gly | Leu | Leu | Lys | Ser | Ser |
| | | | | 245 | | | | | 250 |

( 2 ) INFORMATION FOR SEQ ID NO:9:

( i ) SEQUENCE CHARACTERISTICS:
( A ) LENGTH: 261 amino acids
( B ) TYPE: amino acid
( D ) TOPOLOGY: linear ( i i ) MOLECULE TYPE: protein ( x i ) SEQUENCE DESCRIPTION: SEQ ID NO:9:

| Ile | Asn | Thr | Ile | Thr | Phe | Asp | Ala | Gly | Asn | Ala | Thr | Ile | Asn | Lys | Tyr |
| 1 | | | | 5 | | | | | 10 | | | | | 15 | |

| Ala | Thr | Phe | Met | Glu | Ser | Leu | Arg | Asn | Glu | Ala | Lys | Asp | Pro | Ser | Leu |
| | | | 20 | | | | | 25 | | | | | 30 | | |

| Lys | Cys | Tyr | Gly | Ile | Pro | Met | Leu | Pro | Asn | Thr | Asn | Ser | Thr | Ile | Lys |
| | | 35 | | | | | 40 | | | | | 45 | | | |

| Tyr | Leu | Leu | Val | Lys | Leu | Gln | Gly | Ala | Ser | Leu | Lys | Thr | Ile | Thr | Leu |
| | 50 | | | | | 55 | | | | | 60 | | | | |

| Met | Leu | Arg | Arg | Asn | Asn | Leu | Tyr | Val | Met | Gly | Tyr | Ser | Asp | Pro | Tyr |
| 65 | | | | | 70 | | | | | 75 | | | | | 80 |

| Asp | Asn | Lys | Cys | Arg | Tyr | His | Ile | Phe | Asn | Asp | Ile | Lys | Gly | Thr | Glu |
| | | | | 85 | | | | | 90 | | | | | 95 | |

| Tyr | Ser | Asp | Val | Glu | Asn | Thr | Leu | Cys | Pro | Ser | Ser | Asn | Pro | Arg | Val |

```
                            100                         105                            110
         Ala  Lys  Pro  Ile  Asn  Tyr  Asn  Gly  Leu  Tyr  Pro  Thr  Leu  Glu  Lys  Lys
                        115                          120                 125
         Ala  Gly  Val  Thr  Ser  Arg  Asn  Glu  Val  Gln  Leu  Gly  Ile  Gln  Ile  Leu
              130                          135                      140
         Ser  Ser  Lys  Ile  Gly  Lys  Ile  Ser  Gly  Gln  Gly  Ser  Phe  Thr  Glu  Lys
         145                          150                      155                      160
         Ile  Glu  Ala  Asp  Phe  Leu  Leu  Val  Ala  Ile  Gln  Met  Val  Ser  Glu  Ala
                             165                      170                      175
         Ala  Arg  Phe  Lys  Tyr  Ile  Glu  Asn  Gln  Val  Lys  Thr  Asn  Phe  Asn  Arg
                        180                          185                     190
         Asp  Phe  Ser  Pro  Asn  Asp  Lys  Val  Leu  Asp  Leu  Glu  Glu  Asn  Trp  Gly
                   195                          200                     205
         Lys  Ile  Ser  Thr  Ala  Ile  His  Asn  Ser  Lys  Asn  Gly  Ala  Leu  Pro  Lys
         210                               215                     220
         Pro  Leu  Glu  Leu  Lys  Asn  Ala  Asp  Gly  Thr  Lys  Trp  Ile  Val  Leu  Arg
         225                          230                      235                      240
         Val  Asp  Glu  Ile  Lys  Pro  Asp  Val  Gly  Leu  Leu  Asn  Tyr  Val  Asn  Gly
                             245                      250                      255
         Thr  Cys  Gln  Ala  Thr
                             260
```

( 2 ) INFORMATION FOR SEQ ID NO:10:

( i ) SEQUENCE CHARACTERISTICS:
       ( A ) LENGTH: 259 amino acids
       ( B ) TYPE: amino acid
       ( D ) TOPOLOGY: linear ( i i ) MOLECULE TYPE: protein ( x i ) SEQUENCE DESCRIPTION: SEQ ID NO:10:

```
         Val  Thr  Ser  Ile  Thr  Leu  Asp  Leu  Val  Asn  Pro  Thr  Ala  Gly  Gln  Tyr
         1                    5                        10                      15
         Ser  Ser  Phe  Val  Asp  Lys  Ile  Arg  Asn  Asn  Val  Lys  Asp  Pro  Asn  Leu
                        20                           25                      30
         Lys  Tyr  Gly  Gly  Thr  Asp  Ile  Ala  Val  Ile  Gly  Pro  Pro  Ser  Lys  Glu
                   35                           40                      45
         Lys  Phe  Leu  Arg  Ile  Asn  Phe  Gln  Ser  Ser  Arg  Gly  Thr  Val  Ser  Leu
              50                           55                     60
         Gly  Leu  Lys  Arg  Asp  Asn  Leu  Tyr  Val  Val  Ala  Tyr  Leu  Ala  Met  Asp
         65                           70                      75                      80
         Asn  Thr  Asn  Val  Asn  Arg  Ala  Tyr  Tyr  Phe  Arg  Ser  Glu  Ile  Thr  Ser
                             85                       90                      95
         Ala  Glu  Ser  Thr  Ala  Leu  Phe  Pro  Glu  Ala  Thr  Thr  Ala  Asn  Gln  Lys
                        100                          105                     110
         Ala  Leu  Glu  Tyr  Thr  Glu  Asp  Tyr  Gln  Ser  Ile  Glu  Lys  Asn  Ala  Gln
                        115                          120                     125
         Ile  Thr  Gln  Gly  Asp  Gln  Ser  Arg  Lys  Glu  Leu  Gly  Leu  Gly  Ile  Asp
              130                          135                      140
         Leu  Leu  Ser  Thr  Ser  Met  Glu  Ala  Val  Asn  Lys  Lys  Ala  Arg  Val  Val
         145                          150                      155                      160
         Lys  Asp  Glu  Ala  Arg  Phe  Leu  Leu  Ile  Ala  Ile  Gln  Met  Thr  Ala  Glu
                             165                      170                      175
         Ala  Ala  Arg  Phe  Arg  Tyr  Ile  Gln  Asn  Leu  Val  Ile  Lys  Asn  Phe  Pro
                        180                          185                     190
         Asn  Lys  Phe  Asn  Ser  Glu  Asn  Lys  Val  Ile  Gln  Phe  Glu  Val  Asn  Trp
                   195                          200                     205
```

```
            Lys  Lys  Ile  Ser  Thr  Ala  Ile  Tyr  Gly  Asp  Ala  Lys  Asn  Gly  Val  Phe
                 210                 215                 220

Asn  Lys  Asp  Tyr  Asp  Phe  Gly  Phe  Gly  Lys  Val  Arg  Gln  Val  Lys  Asp
                 225                      230                 235                      240

Leu  Gln  Met  Gly  Leu  Leu  Met  Tyr  Leu  Gly  Lys  Pro  Lys  Ser  Ser  Asn
                              245                      250                      255

Glu  Ala  Asn
```

( 2 ) INFORMATION FOR SEQ ID NO:11:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GGGCTAGATA  CCGTGTCATT  CTCAACCAAA  GGTGCCACTT  ATATTACCTA  CGTGAATTTC    60
TTGAATGAGC  TACGAGTTAA  ATTGAAACCC  GAAGGTAACA  GCCATGGAAT  CCCATTGCTG   120
CGCAAAAAAT  GTGATGATCC  TGGAAAGTGT  TTCGTTTTGG  TAGCGCTTTC  AAATGACAAT   180
GGACAGTTGG  CGGAAATAGC  TATAGATGTT  ACAAGTGTTT  ATGTGGTGGG  CTATCAAGTA   240
AGAAACAGAT  CTTACTTCTT  TAAAGATGCT  CCAGATGCTG  CTTACGAAGG  CCTCTTCAAA   300
AACACAATTA  AACAAGACT   TCATTTTGGC  GGCACGTATC  CCTCGCTGGA  AGGTGAGAAG   360
GCATATAGAG  AGACAACAGA  CTTGGGCATT  GAACCATTAA  GGATTGGCAT  CAAGAAACTT   420
GATGAAAATG  CGATAGACAA  TTATAAACCA  ACGGAGATAG  CTAGTTCTCT  ATTGGTTGTT   480
ATTCAAATGG  TGTCTGAAGC  AGCTCGATTC  ACCTTTATTG  AGAACCAAAT  TAGAAATAAC   540
TTTCAACAGA  GAATTCGCCC  GGCGAATAAT  ACAATCAGCC  TTGAGAATAA  ATGGGGTAAA   600
CTCTCGTTCC  AGATCCGGAC  ATCAGGTGCA  AATGGAATGT  TTTCGGAGGC  AGTTGAATTG   660
GAACGTGCAA  ATGGCAAAAA  ATACTATGTC  ACCGCAGTTG  ATCAAGTAAA  ACCCAAAATA   720
GCACTCTTGA  AGTTCGTCGA  TAAAGATCCT  AAAACGAGCC  TTGCTGCTGA  ATTGATAATC   780
CAGAACTATG  AGTCATTAGT  GGGCTTTGAT  TAG                                  813
```

( 2 ) INFORMATION FOR SEQ ID NO:12:

( i ) SEQUENCE CHARACTERISTICS:
        ( A ) LENGTH: 846 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
ATGGCGGCAA  AGATGGCGAA  GAACGTGGAC  AAGCCGCTCT  TCACCGCGAC  GTTCAACGTC    60
CAGGCCAGCT  CCGCCGACTA  CGCCACCTTC  ATCGCCGGCA  TCCGCAACAA  GCTCCGCAAC   120
CCGGCGCACT  TCTCCCACAA  CCGCCCCGTG  CTGCCGCCGG  TCGAGCCCAA  CGTCCCGCCG   180
AGCAGGTGGT  TCCACGTCGT  GCTCAAGGCC  TCGCCGACCA  GCGCCGGGCT  CACGCTGGCC   240
ATCCGCGCGG  ACAACATCTA  CCTGGAGGGC  TTCAAGAGCA  GCGACGGCAC  CTGGTGGGAG   300
CTCACCCCGG  GCCTCATCCC  CGGCGCCACC  TACGTCGGGT  CGGCGGCAC   CTACCGCGAC   360
CTCCTCGGCG  ACACCGACAA  GCTAACCAAC  GTCGCTCTCG  GCCGACAGCA  GCTGGCGGAC   420
GCGGTGACCG  CGCTCCACGG  GCGCACCAAG  GCCGACAAGG  CCTCCGGCCC  GAAGCAGCAG   480
```

| | | | | | | |
|---|---|---|---|---|---|---|
| CAGGCGAGGG | AGGCGGTGAC | GACGCTGGTC | CTCATGGTGA | ACGAGGCCAC | GCGGTTCCAG | 540 |
| ACGTGTCTG | GGTTCGTGGC | CGGGTTGCTG | CACCCCAAGG | CGGTGGAGAA | GAAGAGCGGG | 600 |
| AAGATCGGCA | ATGAGATGAA | GGCCCAGGTG | AACGGGTGGC | AGGACCTGTC | CGCGGCGCTG | 660 |
| CTGAAGACGG | ACGTGAAGCC | TCCGCCGGGA | AAGTCGCCAG | CGAAGTTCGC | GCCGATCGAG | 720 |
| AAGATGGGCG | TGAGGACGGC | TGAACAGGCC | GCCAACACGC | TGGGGATCCT | GCTGTTCGTG | 780 |
| GAGGTGCCGG | GTGGGTTGAC | GGTGGCCAAG | GCGCTGGAGC | TGTTCCATGC | GAGTGGTGGG | 840 |
| AAATAG | | | | | | 846 |

( 2 ) INFORMATION FOR SEQ ID NO:13:

( i ) SEQUENCE CHARACTERISTICS:
        ( A ) LENGTH: 913 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

| | | | | | | |
|---|---|---|---|---|---|---|
| CGTCCGAAAA | TGGTGAAATG | CTTACTACTT | TCTTTTTTAA | TTATCGCCAT | CTTCATTGGT | 60 |
| GTTCCTACTG | CCAAGGCGA | TGTTAACTTC | GATTGTCGA | CTGCCACTGC | AAAAACCTAC | 120 |
| ACAAAATTTA | TCGAAGATTT | CAGGGCGACT | CTTCCATTTA | GCCATAAAGT | GTATGATATA | 180 |
| CCTCTACTGT | ATTCCACTAT | TTCCGACTCC | AGACGTTTCA | TACTCCTCGA | TCTTACAAGT | 240 |
| TATGCATATG | AAACCATCTC | GGTGGCCATA | GATGTGACGA | ACGTTTATGT | TGTGGCGTAT | 300 |
| CGCACCCGCG | ATGTATCCTA | CTTTTTTAAA | GAATCTCCTC | CTGAAGCTTA | TAACATCCTA | 360 |
| TTCAAAGGTA | CGCGGAAAAT | TACACTGCCA | TATACCGGTA | ATTATGAAAA | TCTTCAAACT | 420 |
| GCTGCACACA | AATAAGAGA | GAATATTGAT | CTTGGACTCC | CTGCCTTGAG | TAGTGCCATT | 480 |
| ACCACATTGT | TTATTACAA | TGCCCAATCT | GCTCCTTCTG | CATTGCTTGT | ACTAATCCAG | 540 |
| ACGACTGCAG | AAGCTGCAAG | ATTTAAGTAT | ATCGAGCGAC | ACGTTGCTAA | GTATGTTGCC | 600 |
| ACTAACTTTA | AGCCAAATCT | AGCCATCATA | AGCTTGGAAA | ATCAATGGTC | TGCTCTCTCC | 660 |
| AACAAATCTT | TTTGGCGCAG | AATCAAGGAG | GAAAATTTAG | AAATCCTGTC | GACCTTATAA | 720 |
| AACCTACCGG | GGAACGGTTT | CAAGTAACCA | ATGTTGATTC | AGATGTTGTA | AAAGGTAATA | 780 |
| TCAAACTCCT | GCTGAACTCC | AGAGCTAGCA | CTGCTGATGA | AAACTTTATC | ACAACCATGA | 840 |
| CTCTACTTGG | GGAATCTGTT | GTGAATTGAA | AGTTTAATAA | TCCACCCATA | TCGAAATAAG | 900 |
| GCATGTTCAT | GAC | | | | | 913 |

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

| | | | |
|---|---|---|---|
| TTYAARGAYG | CNCCNGAYGC | NGCNTAYGAR | GG | 32 |

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

ACYTGRTCNA CNGCNGTNAC RTARTAYTTY TT                                    32

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GGNYTNGAYA CNGTNWSNTT YWSNACNAAR GG                                    32

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

AATGGTTCAA TGCCCAAGTC TGT                                              23

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TGTCTCTCTA TATGCCTTTC CAC                                              23

( 2 ) INFORMATION FOR SEQ ID NO:19:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

TCAACCCGGG CTAGATACCG TGTCATTCTC AACCAAAGGT GCCACTTATA TTA             53

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

CTTCATTTTG GCGGCACGTA TCC                                              23

( 2 ) INFORMATION FOR SEQ ID NO:21:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CTCGAGGCTG CAAGCTTACG TGGGATTTTT TTTTTTTTT TTTTT        46

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

CTCGCTGGAA GGTGAGAA        18

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

CTCGAGGCTG CAAGCTTACG TGGGA        25

( 2 ) INFORMATION FOR SEQ ID NO:24:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

TGATCTCGAG TACTATTTAG GATCTTTATC GACGA        35

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

GTAAGCAGCA TCTGGAGCAT CT        22

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE: DNA (xi) SEQUENCE DESCRIPTION: SEQ ID NO:26:

CATTCAAGAA ATTCACGTAG G                                                                          21

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

GGCCTGGACA CCGTGAGCTT TAG                                                                        23

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TCGATTGCGA TCCTAAATAG TACTC                                                                      25

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TTTAGGATCG CAATCGACGA ACTTCAAG                                                                   28

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GTTCGTCTGT AAAGATCCTA AATAGTACTC GA                                                              32

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GGATCTTTAC AGACGAACTT CAAGAGT                                                                    27

( 2 ) INFORMATION FOR SEQ ID NO:32:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

TCTTGTGCTT CGTCGATAAA GATCC                              25

( 2 ) INFORMATION FOR SEQ ID NO:33:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

ATCGACGAAG CACAAGAGTG CTATTTT                          27

( 2 ) INFORMATION FOR SEQ ID NO:34:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GTAAAACCAT GCATAGCACT CTTGAAGTTC GT                  32

( 2 ) INFORMATION FOR SEQ ID NO:35:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

AGTGCTATGC ATGGTTTTAC TTGATCAACT GC                  32

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

AGCACATGTG GTGCCACTTA TATTACCTA                      29

( 2 ) INFORMATION FOR SEQ ID NO:37:

( i ) SEQUENCE CHARACTERISTICS:
        ( A ) LENGTH: 33 base pairs
        ( B ) TYPE: nucleic acid (C) STRANDEDNESS: single
            (D) TOPOLOGY: linear (ii) MOLECULE TYPE: DNA (xi) SEQUENCE DESCRIPTION: SEQ ID NO:37:

TAAGTGGCAC CACATGTGCT AAAGCTCACG GTG    33

(2) INFORMATION FOR SEQ ID NO:38:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

TGACTGTGGA CAGTTGGCGG AAATA    25

(2) INFORMATION FOR SEQ ID NO:39:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

GCCACTGTCC ACAGTCATTT GAAAGCGCTA CC    32

(2) INFORMATION FOR SEQ ID NO:40:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

GATGATCCTG GAAAGGCTTT CGTTTGGTA GCGCTT    36

(2) INFORMATION FOR SEQ ID NO:41:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:41:

AAGCCTTTCC AGGATCATCA GCTTTTTGG GCAGCAATGG G    41

(2) INFORMATION FOR SEQ ID NO:42:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:42:

AAGCCTTTCC AGGATCATCA CAT                                                                       23

( 2 ) INFORMATION FOR SEQ ID NO:43:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GCGACTCTCT ACTGTTTC                                                                             18

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGTTAGCAAT TTAACTGTGA T                                                                         21

( 2 ) INFORMATION FOR SEQ ID NO:45:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

AACAGCTATG ACCATG                                                                               16

( 2 ) INFORMATION FOR SEQ ID NO:46:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

TGAACTCGAG GAAACTACCT ATTTCCCAC                                                                 29

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

GCATTACATC CATGGCGGC                                                                            19

( 2 ) INFORMATION FOR SEQ ID NO:48:

( i ) SEQUENCE CHARACTERISTICS:
        ( A ) LENGTH: 64 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:48:

GATATCTCGA GTTAACTATT TCCCACCACA CGCATGGAAC AGCTCCAGCG CCTTGGCCAC                60

CGTC                                                                            64

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:49:

TATCTGTTCG TGGAGGTGCC G                                                         21

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:50:

CGTTAGCAAT TTAACTGTGA T                                                         21

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:51:

CCAAGTGTCT GGAGCTGTTC CATGCGA                                                   27

( 2 ) INFORMATION FOR SEQ ID NO:52:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:52:

GATGTTAAYT TYGAYTTGTC NACDGCTAC                                                 29

( 2 ) INFORMATION FOR SEQ ID NO:53:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:53:

ATTGGNAGDG TAGCCCTRAA RTCYTCDAT                                              29

( 2 ) INFORMATION FOR SEQ ID NO:54:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

GCCACTGCAA AAACCTACAC AAAATTTATT GA                                          32

( 2 ) INFORMATION FOR SEQ ID NO:55:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

GATGTTAACT TCGATTTGTC GA                                                     22

( 2 ) INFORMATION FOR SEQ ID NO:56:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

TCAACTCGAG GTACTCAATT CACAACAGAT TCC                                         33

( 2 ) INFORMATION FOR SEQ ID NO:57:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

GGCCTGGACA CCGTGAGCTT TAGCACTAAA GGTGCCACTT ATATTACCTA CGTGAATTTC      60
TTGAATGAGC TACGAGTTAA ATTGAAACCC GAAGGTAACA GCCATGGAAT CCCATTGCTG      120
CGCAAAAAAT GTGATGATCC TGGAAAGTGT TTCGTTTTGG TAGCGCTTTC AAATGACAAT      180
GGACAGTTGG CGGAAATAGC TATAGATGTT ACAAGTGTTT ATGTGGTGGG CTATCAAGTA      240
AGAAACAGAT CTTACTTCTT TAAAGATGCT CCAGATGCTG CTTACGAAGG CCTCTTCAAA      300
AACACAATTA AACAAGACT TCATTTTGGC GGCACGTATC CCTCGCTGGA AGGTGAGAAG       360
GCATATAGAG AGACAACAGA CTTGGGCATT GAACCATTAA GGATTGGCAT CAAGAAACTT      420
GATGAAAATG CGATAGACAA TTATAAACCA ACGGAGATAG CTAGTTCTCT ATTGGTTGTT      480
ATTCAAATGG TGTCTGAAGC AGCTCGATTC ACCTTTATTG AGAACCAAAT TAGAAATAAC      540
TTTCAACAGA GAATTCGCCC GGCGAATAAT ACAATCAGCC TTGAGAATAA ATGGGGTAAA      600

| | | | | |
|---|---|---|---|---|
| CTCTCGTTCC | AGATCCGGAC | ATCAGGTGCA | AATGGAATGT | TTTCGGAGGC AGTTGAATTG | 660
| GAACGTGCAA | ATGGCAAAAA | ATACTATGTC | ACCGCAGTTG | ATCAAGTAAA ACCCAAAATA | 720
| GCACTCTTGA | AGTTCGTCGA | TAAAGATCCT | AAAACGAGCC | TTGCTGCTGA ATTGATAATC | 780
| CAGAACTATG | AGTCATTAGT | GGGCTTTGAT | TAG | | 813